United States Patent
Vuong

(10) Patent No.: US 6,586,257 B1
(45) Date of Patent: Jul. 1, 2003

(54) MULTIWELL SCANNER AND SCANNING METHOD

(75) Inventor: T. Minh Vuong, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 72 days.

(21) Appl. No.: 09/665,546

(22) Filed: Sep. 19, 2000

Related U.S. Application Data

(63) Continuation-in-part of application No. 09/417,246, filed on Oct. 12, 1999, now Pat. No. 6,448,089.

(51) Int. Cl.[7] .............................................. G01N 21/03
(52) U.S. Cl. ....................... 436/165; 436/164; 359/196; 359/197; 359/202
(58) Field of Search ............................... 422/73, 65–67, 422/63, 50, 68.1, 82.05, 100; 435/7.1, 287.1, 288.3, 288.7; 356/244, 442; 436/164, 165; 359/197, 202

(56) References Cited

U.S. PATENT DOCUMENTS

| | | |
|---|---|---|
| 4,061,543 A | 12/1977 | Bean et al. |
| 4,461,403 A | 7/1984 | Kuperstein |
| 4,628,933 A | 12/1986 | Michelson |
| 4,677,989 A | 7/1987 | Robblee |
| 4,969,468 A | 11/1990 | Byers et al. |

(List continued on next page.)

FOREIGN PATENT DOCUMENTS

| | | |
|---|---|---|
| EP | 0 760 478 A2 | 3/1997 |
| WO | WO97/19339 | 5/1997 |
| WO | WO99/04228 | 1/1999 |

OTHER PUBLICATIONS

Laser Displacement Meters–LK series; <http://www.keyence.com/measure/lk.htm>; as of Sep. 6, 2000.

The 6K platform & ordering Information; <http://www.compumotor.com/wwwroot/literature/pg033%5F6k%k5Fplatform.htm>; as of Sep. 18, 2000.

Primary Examiner—Jill Warden
Assistant Examiner—Yelena Gakh
(74) Attorney, Agent, or Firm—Knobbe, Martens, Olson & Bear LLP

(57) ABSTRACT

A multiwell plate scanner comprises a detector for measuring an attribute of a sample which is scanned continuously over wells of a multiwell plate. A signal obtained during the scan may be sampled and digitized based on detector position over the multiwell plate. The scanner is also disclosed for scanning microarrays, bio-chips and areas of samples not having physical separations. The scanner may be used in a high throughput screening system comprising a storage and retrieval module, a sample distribution module, a reagent distribution module, and a detector which incorporates the scanner. The screening system may further comprise a transport module and a data processing and integration module for transporting samples between the components of the system and for controlling system operation. In a further aspect, the present invention comprises methods and apparatus to compensate for variations, inconsistencies and other differences in the dimensions, configuration and/or materials of the platform in which an assay is performed. Another aspect of the invention is a system and method for performing an assay to detect the effect of a reagent on a target. The present invention is also directed to compositions and therapeutics identified by the disclosed methods. A further aspect of the present invention is a method of testing a therapeutic for therapeutic activity and toxicology by identifying a compound using a method of the present invention and monitoring the toxicology and efficacy of the therapeutic in an in vivo model.

22 Claims, 27 Drawing Sheets

U.S. PATENT DOCUMENTS

| | | |
|---|---|---|
| 5,024,223 A | 6/1991 | Chow |
| 5,187,096 A | 2/1993 | Giaever et al. |
| 5,405,367 A | 4/1995 | Schulman et al. |
| 5,416,329 A | 5/1995 | Sonne et al. |
| 5,439,440 A | 8/1995 | Hofmann |
| 5,512,492 A | 4/1996 | Herron et al. |
| 5,545,130 A | 8/1996 | Hofmann et al. |
| 5,563,067 A | 10/1996 | Sugihara et al. |
| 5,569,591 A | 10/1996 | Kell et al. |
| 5,571,158 A | 11/1996 | Bolz et al. |
| 5,677,196 A | 10/1997 | Herron et al. |
| 5,686,300 A | 11/1997 | Berndt |
| 5,770,440 A | 6/1998 | Berndt |
| 5,784,152 A | 7/1998 | Heffelfinger et al. |
| 5,798,263 A | 8/1998 | Wood et al. |
| 5,810,725 A | 9/1998 | Sugihara et al. |
| 5,919,712 A | 7/1999 | Herron et al. |
| 5,935,155 A | 8/1999 | Humayun et al. |
| 5,957,958 A | 9/1999 | Schulman et al. |
| 5,965,452 A | 10/1999 | Kovacs |
| 5,981,268 A | 11/1999 | Kovacs et al. |
| 6,008,038 A | 12/1999 | Kroger et al. |
| 6,009,347 A | 12/1999 | Hofmann |
| 6,010,613 A | 1/2000 | Walters et al. |
| 6,043,066 A | 3/2000 | Mangano et al. |
| 6,071,748 A | 6/2000 | Modlin et al. |
| 6,130,745 A * | 10/2000 | Manian et al. ............ 356/123 |
| 6,309,601 B1 * | 10/2001 | Juncosa et al. ............ 422/50 |

* cited by examiner

FIG. 19 Determining the Read Head's Z-Position

MULTIWELL SCANNER AND SCANNING METHOD

CROSS REFERENCE TO RELATED APPLICATIONS

This is a continuation-in-part of U.S. patent application Ser. No. 09/417,246, filed Oct. 12, 1999, now U.S. Pat. No. 6,448,089. The benefit of the earlier filing date of the aforementioned application is expressly claimed under 35 U.S.C. Section 120 and its disclosure is hereby incorporated by reference in its entirety.

BACKGROUND OF THE INVENTION

1. Field of the Invention

The present invention generally relates to devices and methods for rapidly identifying chemicals with biological activity in liquid samples, particularly automated screening of low volume samples for new medicines, agrochemicals, or cosmetics.

2. Description of the Related Art

Drug discovery is a highly time dependent and critical process in which significant improvements in methodology can dramatically improve the pace at which a useful chemical becomes a validated lead, and ultimately forms the basis for the development of a drug. In many cases the eventual value of a useful drug is set by the timing of its arrival into the market place, and the length of time the drug enjoys as an exclusive treatment for a specific ailment.

A major challenge for pharmaceutical companies is to increase the speed and efficiency of this process while at the same time minimizing costs. One solution to this problem has been to develop high throughput screening systems that enable the rapid analysis of many thousands of chemical compounds per 24 hours. To reduce the otherwise prohibitive costs of screening such large numbers of compounds, typically these systems use miniaturized assay systems that dramatically reduce reagent costs, and improve productivity. To efficiently handle large numbers of miniaturized assays it is necessary to implement automatic robotically controlled analysis systems that can provide reliable reagent addition and manipulations. Preferably these systems and the invention herein are capable of interacting in a coordinated fashion with other systems sub-components, such as a central compound store to enable rapid and efficient processing of samples.

Miniaturized high throughput screening systems require robust, reliable and reproducible methods of analysis that are sensitive enough to work with small sample sizes. While there are a large number of potential analysis methods that can successfully be used in macroscopic analysis, many of these procedures are not easily miniaturizable, or lack sufficient sensitivity when miniaturized. This is typically true because absolute signal intensity from a given sample decreases as a function of the size of the sample, whereas background optical or detector noise remains more or less constant for large or small samples. Preferred assays for miniaturized high throughput screening assays have high signal to noise ratios for very small sample sizes.

Fluorescence based measurements have high sensitivity and perform well with small samples, where factors such as inner filtering of excitation and emission light are reduced. Fluorescence based measurements therefore exhibit good signal to noise ratios even with small sample sizes. A particularly preferred method of using fluorescence based signal detection is to generate a fluorescent (emission) signal that simultaneously changes at two or more wavelengths. A ratio can be calculated based on the emission light intensity at the first wavelength divided by the emitted light intensity at a second wavelength. This ratiometric measurement of a fluorescent assay has several important advantages over other non-ratiometric types of analysis. Firstly, the ratio is largely independent of the actual concentration of the fluorescent dye that is emitting fluorescence. Secondly, the ratio is largely independent of the intensity of light with which the fluorescent compound is being excited. Thirdly, the ratio is largely independent of changes in the sensitivity of the detector, provided that is that these changes are the same for the detection efficiency at both wavelengths. This combination of advantages makes fluorescence based ratiometric assays highly attractive for high throughput screening systems, where day to day, and, assay to assay reproducibility are important.

Traditionally, there are two general ways to read fluorescence from a multi-well plate. In one arrangement, a read head is moved from well to well and at each well, there is a dwell time during which the fluorescence signal is digitized and stored into memory. Optically, this scheme is the simplest. There is only one optical assembly, one set of filters and one detector. However, depending on how many wells there are in the plate, the read time can be unacceptably long. It is not just the dwell times that contribute to the total read time. Every time the read head is moved from well to well, it takes time to accelerate and decelerate the stage used in moving the setup.

In the other arrangement, some sort of parallelism is employed. Either a picture is taken of the plate, using a CCD camera or some other imaging arrangement, or multiple optical read heads are employed. The advantage of this arrangement is a significant reduction in the read time. However, a new difficulty is introduced, namely that of normalization. When several wells are read at the same time by several read heads, the question that arises is how to make sure that these heads behave in the same way in terms of collection efficiency, detector sensitivity, filter quality and the like. In the case of a CCD camera, the analogous issue is one of flat-fielding. Accordingly, improved methods and systems for rapidly and accurately measuring fluorescence signals in high throughput screening environments are needed.

SUMMARY OF THE INVENTION

In one embodiment, a method in accordance with the invention comprises placing a platform on a detector for detecting sample attributes, wherein the detector has an adjustable parameter. The method includes making a plurality of measurements of a characteristic of the platform to obtain a plurality of measured values of the characteristic at different locations on the platform. The attributes are measured with the detector with the parameter adjusted based upon the measured values.

In one embodiment, the platform is a multi-well plate, the characteristic comprises a bottom contour of the multi-well plate, and the adjustable parameter comprises the distance between an optical detector and the multi-well plate bottom. In some of these embodiments, to maintain the optimal distance between the optics and the plate, the detector is provided with a sensor used to detect the location of a plate element of interest. In addition, the optics are mounted on an optics positioning device, for example a linear stage. In one embodiment, the optics positioning device may be oriented in the vertical axis so that the vertical position of the optics may be adjusted relative to the plate. Alternative to adjusting the optics, the plate positioner may be mounted on a stage oriented in the vertical axis and the plate may be moved to adjust the relative position of the plate and optics. The optics positioning device is slaved to the stages on the plate positioner which controls the horizontal position of the plate relative to the optics.

The method of reading a microplate while compensating for plate variations comprises first mapping the topology of the plate element of interest, for example the elevation of the plate bottom relative to the optics. The plate is moved relative to the sensor along all or a representative portion of the plate element of interest. The plate may be moved in any desired pattern which covers the desired area, but is preferably moved in a raster scan. As the plate is moved, the sensor measures the location of the plate element of interest. From these measurements a contour map of the plate element of interest may be computed which describes the plate topology. After the mapping is complete, the scanner reads the plate. During the reading scan, the optics positioning device adjusts the positioning of the optics based upon the mapped plate topology to maintain the desired distance between the optics and the critical plate element. For example, the optics positioning device may adjust the distance between the optics and the bottom of the plate to maintain a substantially constant distance between the optics and the bottom of the plate as each of the wells is scanned. In some advantageous embodiments, the reading scan is performed in an essentially continuous fashion along rows of wells, avoiding dwell time on each well and thereby decreasing the time required to scan a multi-well plate.

In another embodiment, an apparatus for detecting an attribute of a plurality of samples disposed on a platform comprises a platform positioning stage for supporting the platform and for aligning a predetermined location of the platform with a predetermined position. The apparatus further comprises a first sensor which measures a feature of the platform at a plurality of different locations and transmits the measured values to a controller. A detector is provided having a signal output representative of the attribute, wherein the detector is positioned to detect the attribute of a sample when the sample is aligned with the predetermined position, and wherein the detector has optics for receiving light transmitted from the samples and the optics are mounted on an optics positioning device. In addition, a controller is adapted to receive the measured values and to transmit a signal to an optics positioning device to control the position of the optics relative to the platform, wherein the optics positioning device is adapted to automatically adjust the position of the optics relative to the platform in response to a signal from the controller based upon the measured values.

Other embodiments of the invention include methods of identifying a chemical having modulating activity with respect to a target molecule. In one specific embodiment, such a method comprises retrieving a plurality of sample chemicals from a chemical storage and retrieval module, placing the plurality of sample chemicals in respective wells of a multiwell plate; routing the multiwell plate to an automated analysis system comprising a detector adapted to measure an attribute of a chemical, biological or biochemical sample, wherein the detector has a detection head, an adjustable parameter and a sensor for measuring a feature of the multiwell plate. The multi-well plate is placed on the detector, and a plurality of measurements are made with the sensor of the feature at or proximate to a plurality of predetermined locations on the multiwell plate. This particular method additionally comprises measuring, with the detector, an attribute of the samples in each predetermined well with the adjustable parameter adjusted based upon the measured value of the feature at the predetermined location at or proximate to each predetermined well so as to obtain measured attribute values for each sample. The measured attribute values are analyzed to detect the modulating activity.

Furthermore, another embodiment of the invention comprises a medicament made by a process comprising identifying a pharmacologically active chemical by a process including loading chemicals into a plurality of wells of a multiwell plate, placing the multiwell plate in a detector adapted to measure an attribute of a chemical, biological or biochemical sample, the detector having a detection head, an adjustable parameter and a sensor for measuring a feature of the multiwell plate, and making a plurality of measurements with the sensor of the feature at or proximate to a plurality of predetermined locations on the multiwell plate to obtain a measured value of the feature at each of the predetermined locations, each of the predetermined locations being at or proximate to a predetermined well of the multiwell plate. The method also comprises measuring, with the detector, an attribute of the samples in each predetermined well with the adjustable parameter adjusted based upon the measured value of the feature at the predetermined location at or proximate to each predetermined well, thereby detecting pharmacological activity of at least one of the samples and incorporating an effective amount of at least one of the pharmacologically active samples into a biocompatible carrier.

DETAILED DESCRIPTION OF THE INVENTION

Figure 1:
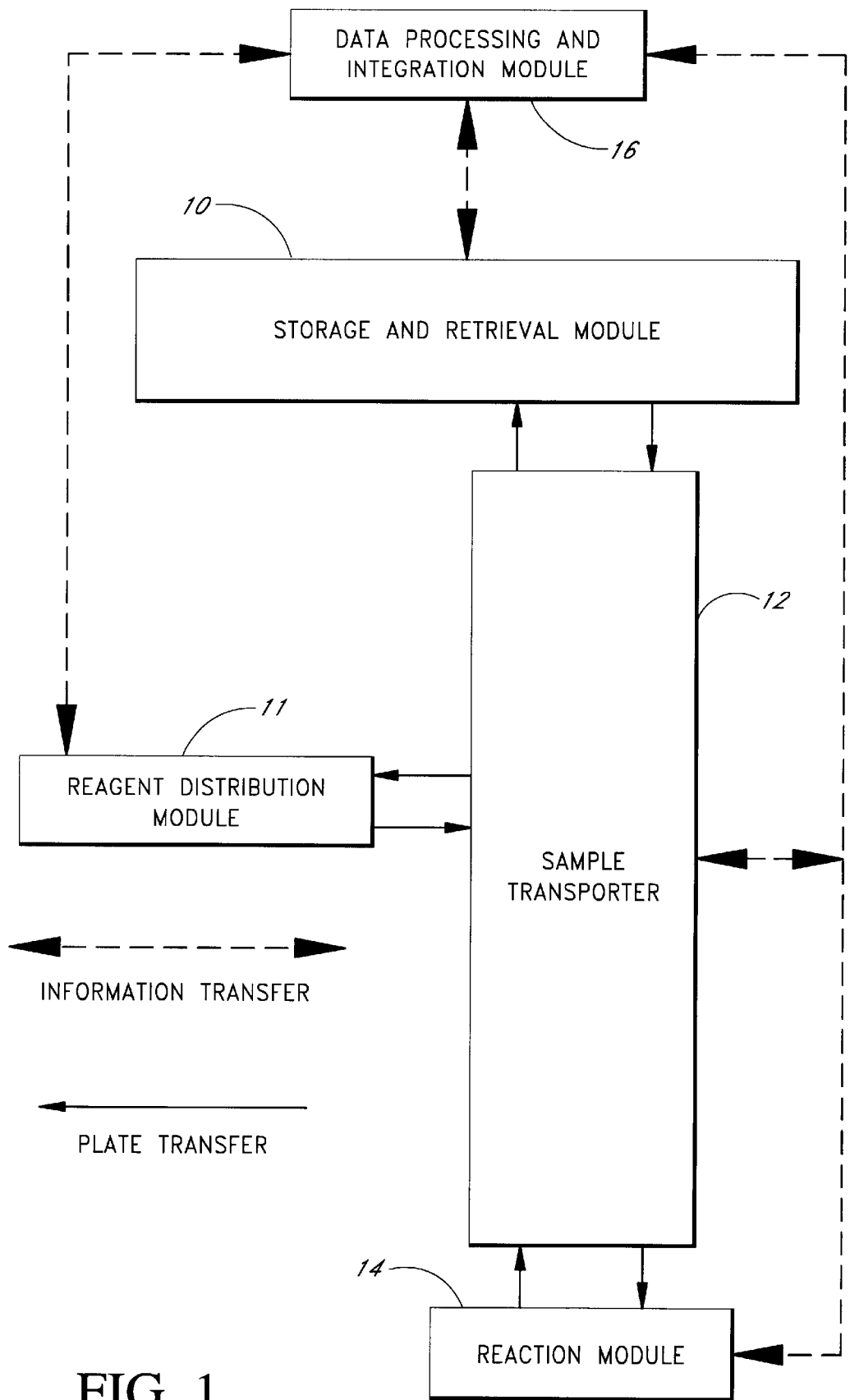
FIG. 1 is a block diagram of a high throughput chemical screening system in accordance with the present invention.

Embodiments of the invention will now be described with reference to the accompanying Figures, wherein like reference numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Unless otherwise defined, all technical and scientific terms used herein have the same meaning as commonly understood by one of ordinary skill in the art to which the invention belongs. Generally, the nomenclature used herein and many of the automation, computer, detection, chemistry and laboratory procedures described below are those well known and commonly employed in the art. Standard techniques are usually used for engineering, robotics, optics, molecular biology, computer software and integration. Generally, chemical reactions, cell assays and enzymatic reactions are performed according to the manufacture's specifications where appropriate. The techniques and procedures are generally performed according to conventional methods in the art and various general references. The reader may see generally Lakowicz, J. R. Principles of Fluorescence Spectroscopy, New York:Plenum Press (1983), and Lakowicz, J. R. Emerging Applications of Fluorescence Spectroscopy to Cellular Imaging: Lifetime Imaging, Metal-ligand Probes, Multi-photon Excitation and Light Quenching, Scanning Microsc. Suppl VOL. 10 (1996) pages 213–24, for fluorescent techniques, Sambrook et al Molecular Cloning: A laboratory manual, $2^{nd}$ ed. (1989) Cold Spring Harbor Laboratory Press, Cold Spring Harbor, N.Y. for molecular biology methods, Optics Guide 5 Melles Griot® Irvine Calif. for general optical methods, Optical Waveguide Theory, Snyder & Love, published by Chapman & Hall, and Fiber Optics Devices and Systems by Peter Cheo, published by Prentice-Hall for fiber optic theory and materials.

As employed throughout the disclosure, the following terms, unless otherwise indicated, shall be understood to have the following meanings:

"Multiwell plate" or "microplate" refers to a two dimensional array of sample wells located on a substantially flat surface. Multiwell plates may comprise any number of separate sample wells, and comprise sample wells of any width or depth. Common examples of multiwell plates include 96 well plates, 384 well plates, 1536 well plates and 3456 well plates, such as those disclosed in commonly assigned U.S. patent application Ser. No. 09/028,283, entitled "Low Fluorescence Assay Platforms Having Greater Than 864 Wells and Related Methods for Drug Discovery," the content of which is hereby incorporated by reference in its entirety.

"Pharmaceutical agent or drug" refers to a chemical compound or composition capable of inducing a desired therapeutic effect when properly administered to a patient.

As used herein, "optical property" refers to a measurable attribute of a sample, such as the intensity of emitted light at a particular wavelength, the intensity or degree of light polarization, the transmittance of a compound or composition, or the reflectance of a compound or composition.

"Ball lens" refers to a sphere, truncated sphere, cylinder, or truncated cylinder of suitable transparent refractive material and is usually a sphere.

"Operably linked" refers to a juxtaposition wherein the components so described are in a relationship permitting them to function in their intended manner.

"Hit" refers to a sample identified as having significant interest or identified as showing that a reagent has had a significant effect on a target.

"Raster scan" refers to a scan pattern in which an area is scanned from side to side in lines succeeding from row to row or column to column, or any combination thereof.

The present invention is directed to improving the speed and accuracy of detection and measurement of light emitted from the sample wells of a multiwell plate. Some aspects of the invention are directed to methods and apparatus to compensate for variations, inconsistencies and other differences in the dimensions, configuration and/or materials of the platform in which an assay is performed. One embodiment of this aspect of the invention comprises an apparatus and method to maintain an optimal distance between the detector optics and a critical plate element, such as the bottom of the multiwell plate (the bottom being used as an indicator for the location of a sample in the associated wells). This capability can be used to compensate for the differences in plate dimensions, including differences among the various formats of plates, differences between various manufacturers and also inconsistencies and lack of flatness in panes of the same format from the same source. For example, some microplates have bottoms which are bowed by as much as 0.5 mm or more. As the density of the wells in a plate increases, flatness becomes ever more important because the amount of sample contained in a well is decreased. As a result, the signal from a sample is likewise decreased. To maximize light collection, the numerical aperture must be increased, but this necessarily results in a very shallow depth of focus. Therefore, the reading optics' depth of focus may not be sufficient to account for irregularities in plate dimension from plate to plate and from well to well within a single plate. The invention finds especially advantageous application to high throughput screening systems (HTSS) where large numbers of compounds are tested for biological or chemical activity, preferably as quickly as possible.

Typically, a system utilizing aspects of the present invention would include most or all of the components used in processing liquid samples to identify a useful chemical, starting with a large store of different reagents (usually liquid) through the later stage processing steps, such as chemical reactions and detection of an analyte or measurement of a physical property of a sample, as well as a component to collect information resulting from such a process. Such a system, as shown in FIG. 1, usually includes the following components:

(1) a storage and retrieval module 10 for storing and retrieving very large numbers (at least about 100,000) of different reagents in containers, (2) a sample distribution module 11 to handle (e.g., aspirate samples from containers and dispense samples into sample containers) small volumes of liquids at a high rate of speed, (3) a sample transporter 12 to transport reagents from a selected component to another at a compatible throughput rate, (4) a reaction module 14 (e.g., a reagent dispenser and a detector) for chemical reactions or physical measurements at high throughput rates, and (5) a data processing and integration module 16 that can control module operation.

If desired, each separate module is integrated and programmably controlled to facilitate the rapid processing of liquid samples, as well as being operably linked to facilitate the rapid processing of liquid samples. One such system is described in U.S. Pat. No. 5,985,214 to Stylii et al., entitled "Systems and Methods for Rapidly Identifying Useful Chemicals in Liquid Samples" which is hereby incorporated by reference in its entirety.

Figure 2:
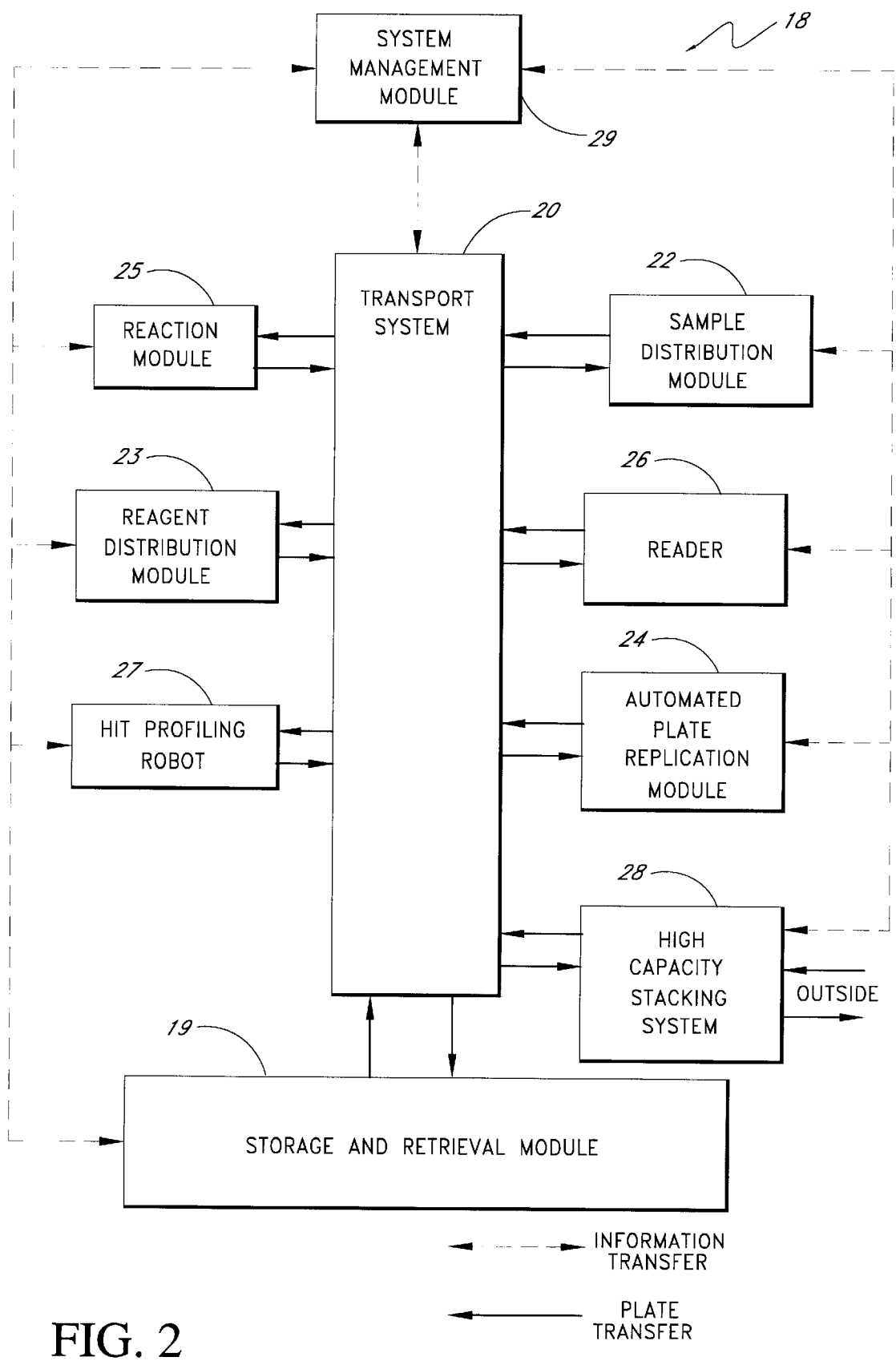
FIG. 2 is a block diagram of another high throughput chemical screening system in accordance with the present invention.

FIG. 2 shows another high throughput screening system 18 according to the present invention. Like the system shown in FIG. 1, the HTSS 18 comprises a storage and retrieval module 19. The HTSS 18 further comprises a sample distribution module 22, a reagent dispensing module 23, an automated plate replication module 24, a reaction module 25, a reader 26, a hit profiling robot 27, a high capacity stacking system 28, and a transport system 20 which operably links each of the modules. A system management module 29 is operably linked to each of the components and modules to provide system operation control and integration and data management.

The storage and retrieval module 19 fully automates storage and delivery of reagents in platforms (such as multiwell plates) for assay procedures. The storage and retrieval module 19 is contemplated to include robotics, instrumentation, electro-mechanical devices, computer equipment and related software that fully automates reagent storage and retrieval and delivery from the storage and retrieval module 19 to the transport system 20. The storage and retrieval module may be substantially as described in U.S. Pat. No. 5,985,214 referenced above.

The transport system 20 comprises apparatus and controls for managing and moving plates between each of the HTSS 18 modules. The transporter system 20 may be substantially as described in application Ser. No. 08/858,016 referenced above.

The hit profiling robot 27 formats plates that are generated from consolidation of hits from separate plates having wells that have been assayed. In operation of the HTSS 18 to perform assays on a number of multiwell plates, wells exhibiting screening hits are typically sparsely distributed among numerous multiwell plates. Of course, a plate may contain none, one or more than one hit identified by a specific assay. The hit profiling robot 27 gathers the hits and groups them together into new destination multiwell plates.

The automated plate replication module 24 reformats samples between multiwell plates. For example, the automated plate replication module 24 can dispense samples from a 384-well plate into a set of four 96-well plates. Alternatively, the automated plate replication module 24 may be configured to dispense samples from the wells of several different 384-well plates into a single 384-well plate. In addition to formatting plates for use in performing automated assays, the automated plate replication module 24 can perform several other useful tasks. For example, it can be used to format sample plates for input into the storage and retrieval module 19. It can also be used to format assay plates for assays performed independent of the HTSS 18.

The sample distribution module 22 dispenses samples from multiwell sample plates into assay plates to be tested. The sample plates will typically be multiwell plates directly from the storage and retrieval module 19 or they may be reformatted plates from the automated plate replication module 24. The sample plates are transported from the storage and retrieval module 19 and/or the automated plate replication module 24 to the sample distribution module 22 on the transport system 20. The assay plates may be very high density plates such as 3456-well plates. Suitable sample distribution modules 22 are disclosed in commonly assigned, co-pending U.S. application Ser. No. 09/210,260, the disclosure of which is hereby incorporated by reference in its entirety.

The reagent dispensing module 23 dispenses reagent into multiwell plates which have been previously formatted with samples by the sample distribution module 22. The reagent dispensing module 23 may be substantially the same as the corresponding apparatus disclosed in pending U.S. application Ser. No. 08/858,016 referenced above.

The high capacity stacking system 28 provides a buffer for short term, temporary storage and retrieval of plates. The high capacity stacking system 28 can be used for bulk loading and unloading of sample plates, storage plates, assay plates and empty plates. Pending U.S. application Ser. No. 08/858,016 describes one such high capacity stacking system.

The reaction module 25 provides a temporary repository with controllable environmental condition that are conducive to the reaction of the particular assay. In one preferred form, the reaction module 25 may comprise an incubator having an automated plate handling subsystem.

The reader 26 comprises a detector such as the fluorescence detector described below. As with all of the modules of the HTSS 18, the reader 26 includes an automated plate handling subsystem for receiving from, and sending plates to, the transport system 24 and for manipulating plates within the module.

The system management module 29 preferably comprises a microcomputer operably linked to each of the components and modules to provide system operation control and integration and data management. A description of a suitable system management module 29 is provided in application Ser. No. 08/858,016 referenced above.

Figure 3:
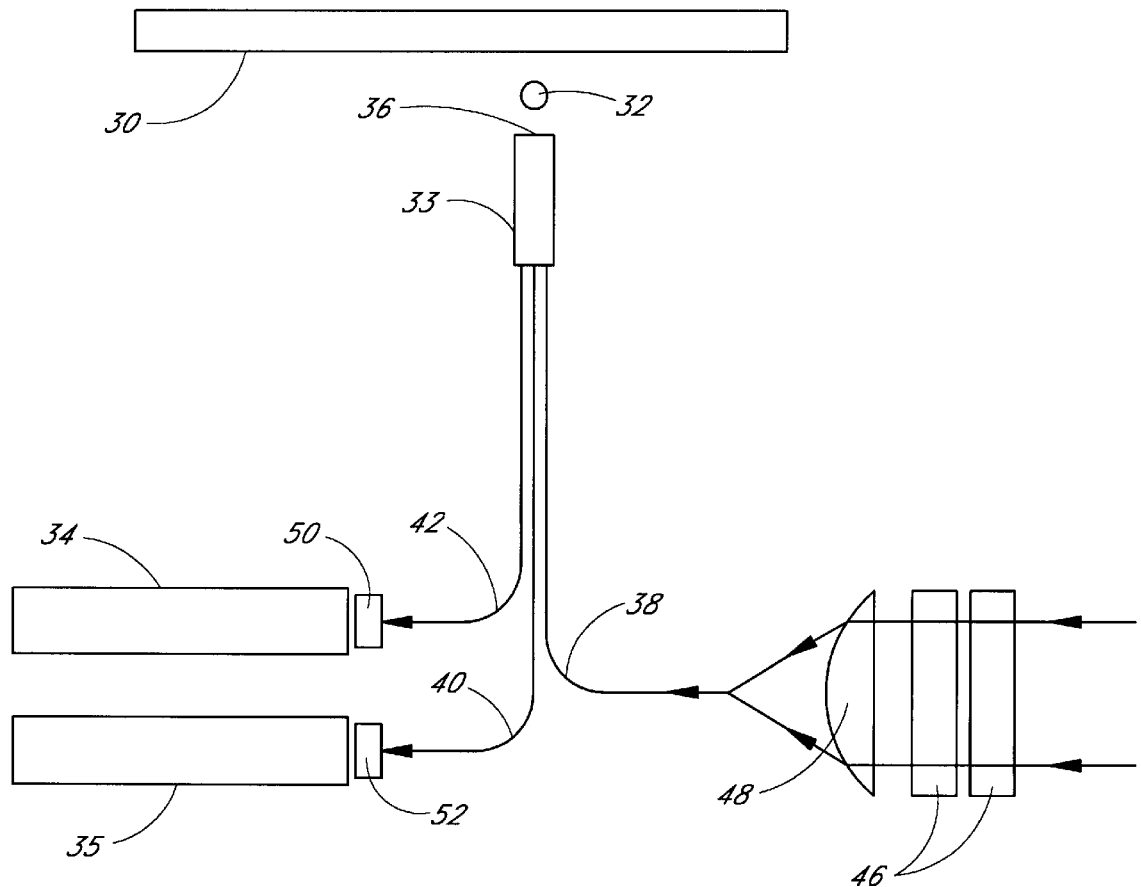
FIG. 3 is a schematic of a fluorescence excitation and emission detection system which may be part of the reaction module of the system of FIG. 1 or part of the reader of the system of FIG. 2.

FIG. 3 illustrates several components of one embodiment of a detector in a reaction module 14 (FIG. 1) or reader 26 (FIG. 2). In the embodiment described in detail herein, the detector is adapted to measure sample fluorescence at two different wavelengths. It will be appreciated, however, that the principles of the present invention may be applied to the detection and/or measurement of any optical property of a sample, and that fluorescence measurement is only one example in which the invention finds especially advantageous application. Furthermore, the scanning apparatus and methods disclosed herein are contemplated for use with measurement devices other than optical sensors, including, but not limited to, radioactivity sensors, temperature sensors, magnetic sensors, and other electromagnetic measurement devices.

Referring again to FIG. 3, a multiwell plate 30 is mounted on a movable positioning stage. A light collector assembly, which may comprise a ball lens 32 and a fiber optic bundle 33, is positioned adjacent to a surface of the multiwell plate. Plates containing aqueous solutions of chemicals, cell suspensions, and compounds are loaded into the reaction module either manually or by a computer-controlled arm.

The multiwell plate 30 is clamped firmly in place on the plate positioner, which may be moved in the x- and y-directions by two motorized linear stages that are orthogonally bolted together. In a further aspect, the plate positioner may allow for movement in the vertical or z-direction using another motorized linear stage. The stages are equipped with high-resolution linear encoders and driven by stepping motors. Three precision manual linear stages allow the tip 36 of the fiberoptic bundle 33 to be positioned in the x-, y- and z-directions with respect to the ball lens 32. The entire light collector assembly may in turn be mounted on a manual stage so that its vertical position with respect to the bottom of the multiwell plate can be precisely adjusted. With this design, it is possible to center the tip of the bundle 33 with respect to the center of the ball lens; focus the excitation light by the ball lens; and also vertically position the entire light collector assembly with respect to the bottom of the multiwell plate.

In one suitable embodiment, the ferrule of the fiber bundle 33 is mounted on one stage, which allows its vertical distance to the ball lens to be adjusted. The ball lens holder is mounted on two orthogonal stages, which allow its center to be lined up with the central excitation fiber (designated 54 in FIG. 4) of the bundle. Depending upon how far the tip 36 of the bundle is from the ball lens 32, the excitation beam is substantially collimated. There is no focused point and the beam is slightly diverging. From 4 mm to 6 mm, there is a focused spot whose diameter is about 150 $\mu$m. The highest signal-to-background ratio is obtained when the fiber tip-to-ball lens distance is 4 mm and the excitation beam is focused. As mentioned above, the entire light collector assembly is mounted on a fourth linear stage so that its vertical distance with respect to the bottom of the multiwell plate 30 can be adjusted. This adjustment is most needed when the excitation beam is focused because the beam spot is optimally positioned within the well. This is especially true when samples containing cells are used. Cells typically form a mono-layer at the bottom of the wells so the relative position of the beam spot relative to this layer has large effects on how well the cells are illuminated and hence on the amplitude of the fluorescence signal.

In the embodiment of FIG. 3, the multiwell plate is moved in the horizontal x-y plane with respect to the remainder of the system while the light collector remains stationary with respect to the remainder of the system to avoid disturbing the positioning of the fiber optic light collection apparatus. It will be appreciated, however, that a moving light collector and stationary multiwell plate may also be utilized to provide the relative motion used to scan the wells of the plate for fluorescence. Thus, the terminology "moving a light collector relative to a plate" and "moving a plate relative to a light collector" are intended to be synonymous and cover both moving plates and moving light collectors as referenced to the remainder of the stationary screening apparatus.

In the embodiment of FIG. 3, two photomultiplier tubes 34, 35 are used to detect fluorescence present in the wells of the multiwell plate, allowing for emission ratio detection. A blue-sensitive bi-alkali photomultiplier tube is typically used to detect the shorter wavelength emission (300 to 650 nm) while a multi-alkali photomultiplier tube is used to detect longer wavelength emission (300 to 850 nm).

Light emitted by fluorescent chemical species is collected through the transparent bottom of microplate wells by the common end 36 of the trifurcated optical fiber bundle 30. One leg 38 of the trifurcated fiber bundle is used as an excitation source. The other two legs 40, 42 of the trifurcated fiber are used to detect fluorescence emission. The common end 36 of the trifurcated bundle 33 is thus used to both excite and collect fluorescence emission.

A 300 watt xenon arc lamp such as the CXP300, ILC Technology, Sunnyvale, Calif., with a parabolic reflector can be used as the fluorescence excitation source. The excitation light is filtered by two 2" diameter interference filters 46 (e.g. 400RDF15 or 480RDF20, Omega Optical, Brattleboro, Vt.). This double filtering minimizes the leakage of white light into the excitation path due to pinhole defects in each individual filter.

The excitation light is then focused by a lens 48 on to the excitation leg of the trifurcated bundle. Both an IR heat absorbing water filter and shutter system may be included in the optical path to protect the interference filters from heat damage. One inch diameter "head-on" photomultiplier (e.g. HC124 series, Hamamatsu Corp, Bridgewater, N.J.) tubes may used to detect the fluorescence emission. Emission interference filters 50, 52 may also be provided at the inputs of the photomultiplier tubes 34, 35.

The fiber optic bundle 33 may be constructed with a wide variety of packing patterns of excitation and emission bundle numbers and arrangements, and with different numbers of fibers in the excitation legs and emission legs. In one embodiment, the packing of the fibers of both the excitation and emission legs in the bundle is random. In another embodiment the fibers are arranged in specific and defined patterns, that confers a preferred optical characteristic to the system. For example, in one preferred embodiment discussed above, the excitation fibers could be bundled together centrally in the fiber optic bundle and the emission filters arranged around the outside to create a coaxial fiber optic bundle. Both bifurcated and trifurcated fiber bundles can be produced in this preferred configuration. Alternatively, the emission bundles could be arranged in small groups to create an array, or radially around the axis of the bundle, or any other symmetrical or non-symmetrical pattern.

Figure 4:
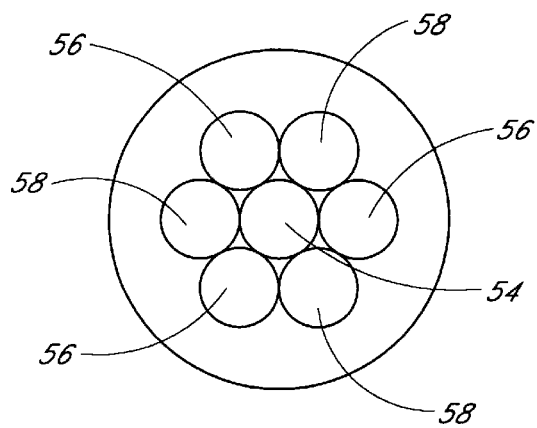
FIG. 4 is a diagram of the trifurcated fiber optic bundle of FIG. 3.

FIG. 4 illustrates one possible configuration of seven fibers. A central fiber 54 comprises the excitation leg. Each emission leg 40, 42 comprises three fibers. At the common end 36 of the bundle, the three fibers of each leg alternate around the central fiber 54. Thus, the three fibers 56 forming one emission leg 40 and the three fibers 58 forming the other emission leg 42 reside at the vertices of equilateral triangles around the central fiber 54. The construction and testing of a fiber bundle/ball lens and several embodiments are also described in commonly assigned, co-pending application Ser. No. 09/122,544, the content of which is hereby incorporated by reference in its entirety.

As illustrated in FIG. 3, a single head strategy is adopted in one embodiment of the invention to avoid the potential difficulty of normalization. However, as the number of wells being scanned increases, the classic move-and-dwell strategy is unable to provide the high throughput rates desired. Instead, the plate may be scanned continuously without coming to a stop over the wells, and thus the wells where the fluorescence samples are contained, as well as the plastic areas between wells, may be read by the optics. This technology therefore allows a high throughput while avoiding the complication of normalization among multiple light collectors.

Figure 5:
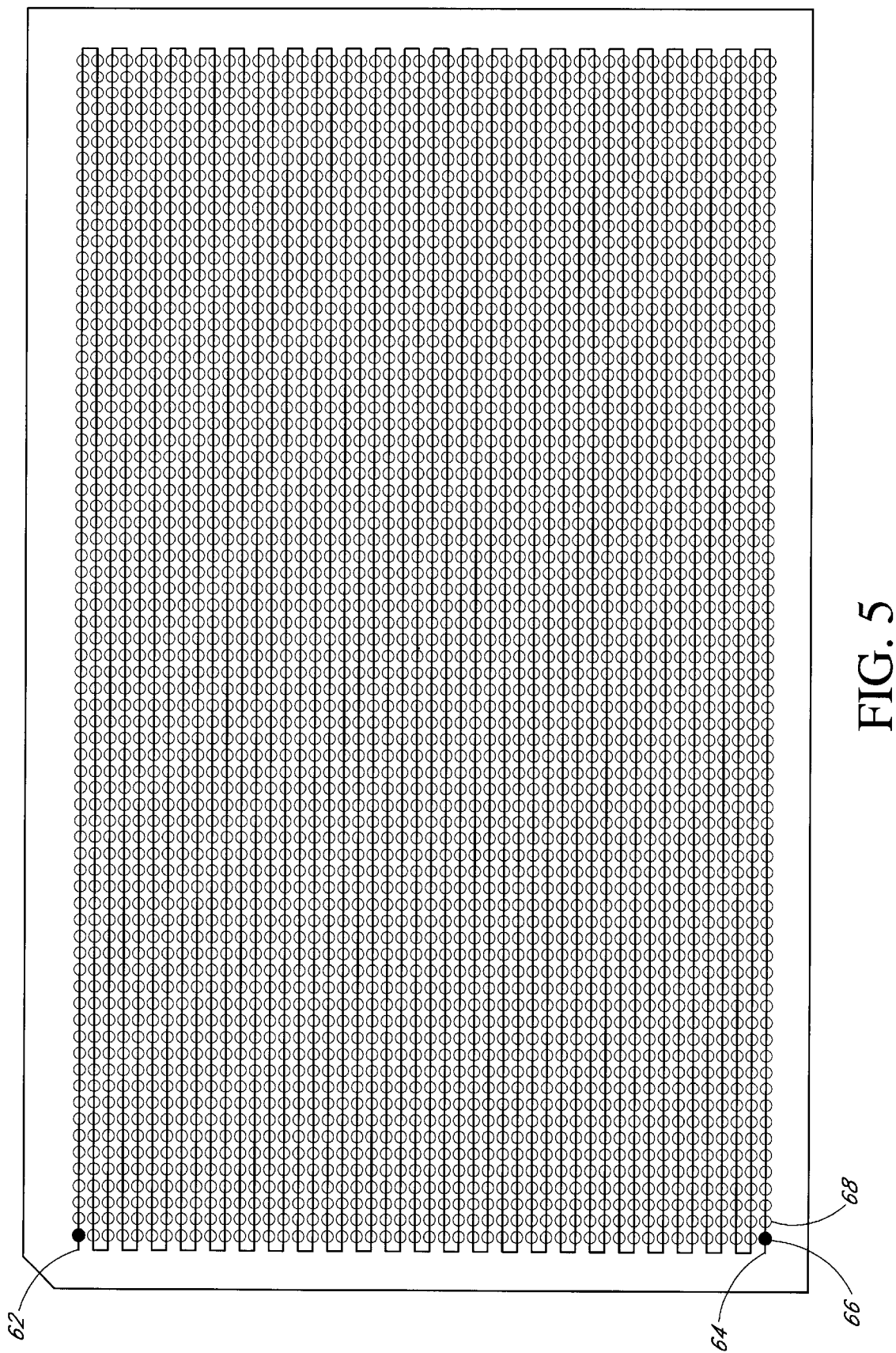
FIG. 5 is a diagram of one embodiment of a light detector scan path in accordance with the invention.

In one embodiment, the multiwell plate is scanned along its long axis in a raster scan as shown in FIG. 5. The multiwell plate typically comprises black plastic forming a two dimensional array of cylindrical wells with transparent plastic bottom surfaces. Thus, each scan of a row starts in the black, "non-well" area 62 on one side of the plate and ends in its counterpart non-well area 64 on the other side. Little light is expected whenever the light collector is under these black areas, which are also present between wells. Much more light is collected when the light collector passes under a well that contains a fluorescence sample.

In contrast to the move and dwell method, where the light collector stops over each well to detect fluorescence, the light collector in this embodiment of the invention continues moving as it passes the first edge of a well 66, over the well itself, and then past the second edge of the well. This continues over a second well 68, and then down a complete row of wells without coming to a stop.

The benefits of this method increase as the wells per plate increases. In the embodiment of FIG. 5, the plate comprises 48 rows of 72 wells each, for a total of 3456 wells. There are three limitations which determine how fast a multiwell plate can be scanned. First, a typical motorized stage can be safely moved without fear of stalling at about 300 mm/sec. Second, the faster the plate is moved, the less light that can be collected by the light collector. In the limit, there is a point when the plate is moved so fast that the photomultiplier tube becomes light-limited, i.e. its dark noise becomes comparable to the light signal. Third, if the wells contain cells, they may be unpredictably jostled due to the hard acceleration and deceleration of a fast moving stage. It has been found that the 3456 well plate of FIG. 5 can be scanned at up to about 90 mm/sec with an acceleration of up to about 1,500 mm/sec$^2$. Because throughput increases as speed and acceleration increase, it is thus advantageous to accelerate and decelerate the plate at about 1000–1500 mm/sec$^2$, and to reach a cruising speed over the wells of about 70–90 mm/sec. With these values, it takes about one minute to complete a scan of a multiwell plate having 3456 wells, and cell samples are not significantly disturbed.

Figure 6:
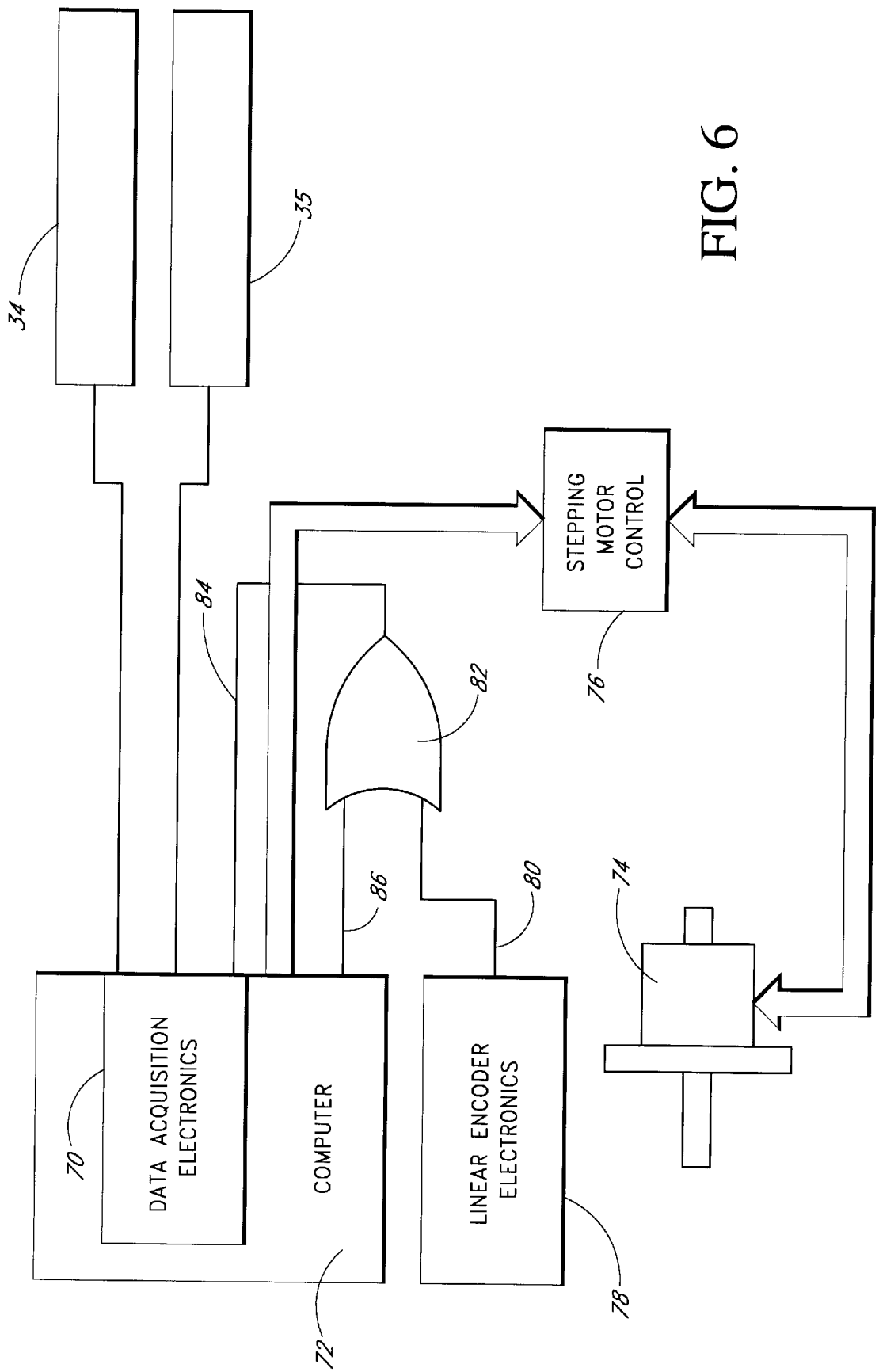
FIG. 6 is a schematic of the data acquisition control electronics in one embodiment of the invention.

A schematic of the fluorescence data collection electronics is illustrated in FIG. 6. Referring now to this Figure, the analog outputs of the two photomultiplier tubes 32, 34 are routed to data acquisition electronics 70 in a computing device 72. For example, data may be collected by a multifunction laboratory data collection circuit card in a Pentium™ based personal computer. The data acquisition electronics 70 performs analog to digital conversion and provides the data to the computer system 72 for storage, analysis, and display.

The relative position of the light collector assembly and the multiwell plate is controlled with stepping motors. The motor 74 which controls movement in the dimension of the well rows is illustrated in FIG. 6. This motor 74 is controlled by a stepping motor controller 76. Movement of the plate is detected by a linear encoder 78, which has an output 80 comprising a series of pulses representative of a corresponding series of incremental position shifts between the light detector and the multiwell plate.

In typical move and dwell schemes, digitization of the analog photomultiplier output is performed as a function of time. At each fixed interval in time, the analog signal is sampled and digitized. In the present case, this simple arrangement is not applicable because the motorized linear stage must ramp up to its final speed at the beginning of each scan, then ramp down to zero at the end. Thus, during a significant portion of the scan, the plate does not move at a constant speed and a time-based digitization would introduce errors at the beginning and end of the data set. To avoid this problem, pulses from the linear encoder are used to trigger the digitization. Every time the linear stage moves a distance of about 2 $\mu$m, the linear encoder generates a TTL pulse, a process that is entirely independent of the speed and acceleration of the stage. This TTL pulse is routed to the data acquisition board to trigger signal sampling and digitization of the analog signals from the photomultiplier tubes 32, 34. When analog signal sampling is position-based rather than time-based, there is no distortion introduced into the data set when the stage undergoes acceleration and deceleration to and from its constant cruising speed. Furthermore, if the same plate is scanned twice with two very different speed profiles, the two data sets obtained are identical.

With this position-based acquisition scheme, however, even when the motorized stage is not commanded to move, it is not completely standing still due to small mechanical perturbations coming from uncontrollable sources such as building vibrations. This means that spurious encoder pulses are constantly and randomly generated as the stage servos back to its original position after each disturbance. Prevention of data acquisition triggering by these spurious encoder pulses is achieved by routing the encoder output 80 to a gate 82, illustrated in FIG. 6 as a NOR gate, although it will be appreciated that a wide variety of logic implementations of the gate 82 are possible. Rather than using the output of the encoder 78 directly to trigger signal sampling, the output 84 of the gate 82 is routed to the data acquisition electronics to provide trigger pulses.

When the stage is idle and no data acquisition is to be performed, a gating signal 86 from the computer 72 is held at logic high, and no trigger pulses reach the data acquisition circuit 84 because the output of NOR gate 82 is forced low, regardless of the presence of pulses at the output 80 of the encoder 78. At the start of a scan, the gate signal 86 is brought low. When the gate signal 86 is low, pulses at the encoder output are passed to the gate output 84 (although inverted in the NOR gate implementation of FIG. 6), and trigger pulses thus reach the data acquisition circuit.

Figure 7:
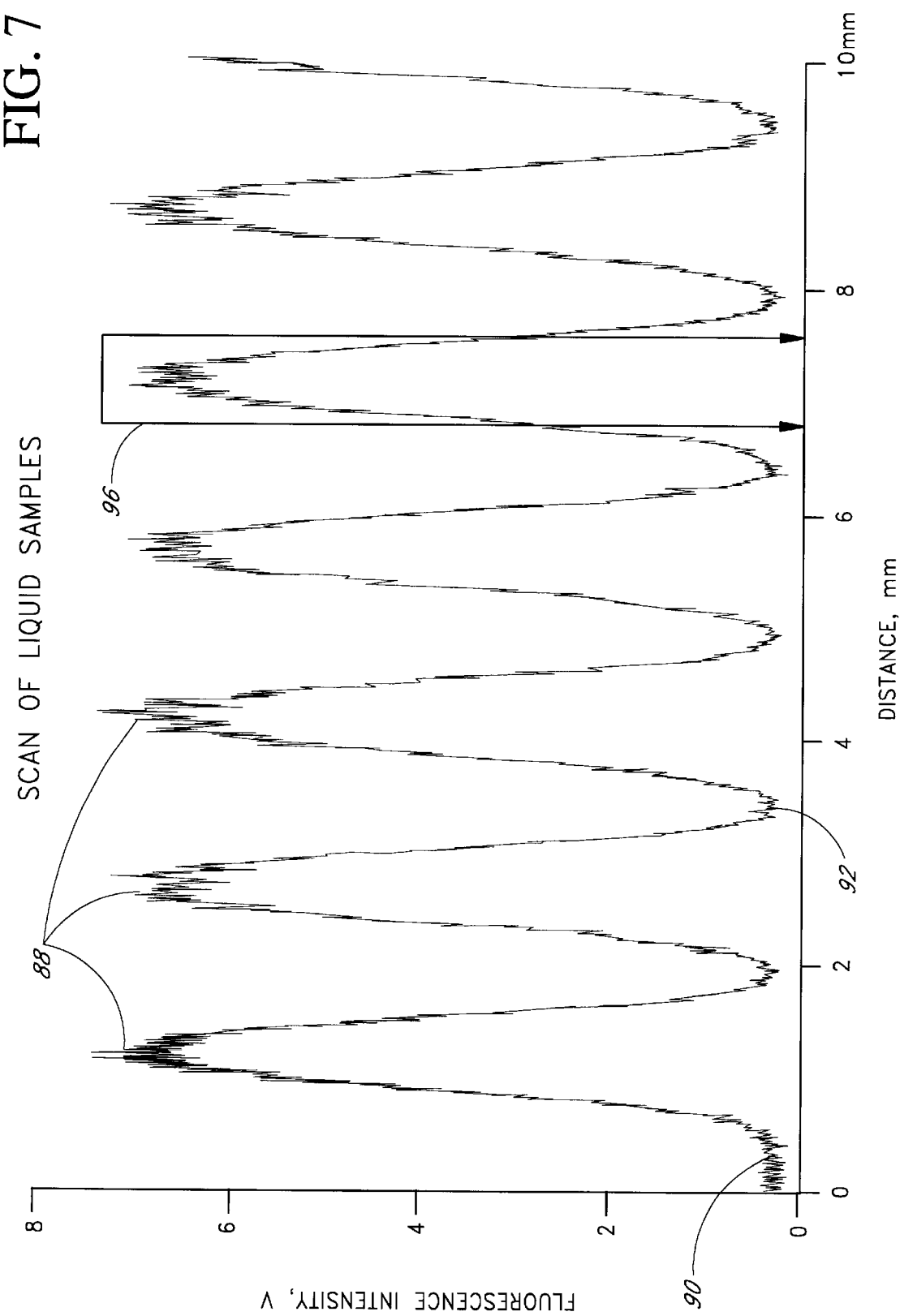
FIG. 7 is a plot of collected light intensity as a function of position during a portion of a scan of wells containing an aqueous chemical solution including fluorescent species.

Raw data obtained with the scanning method described above is shown in FIGS. 7 and 8. Each scan of a seventy-two well row results in seventy-two peaks 88. The fluorescence intensities in the area 90 before the first well and in the area 92 between adjacent wells are about equal. When the light collector is under the area 90 before the first well, it is safely far away from all fluorescence samples and the intensity obtained there may be taken as a background value. Thus, when the light collector is in between adjacent wells, the intensity obtained is also essentially a background value. This finding demonstrates that there is no cross-talk between adjacent wells, and that when the light collector is between wells, it no longer samples any fluorescent light from the samples, only the background from the plastic body, which is further minimized with the use of black plastic.

Figure 8:
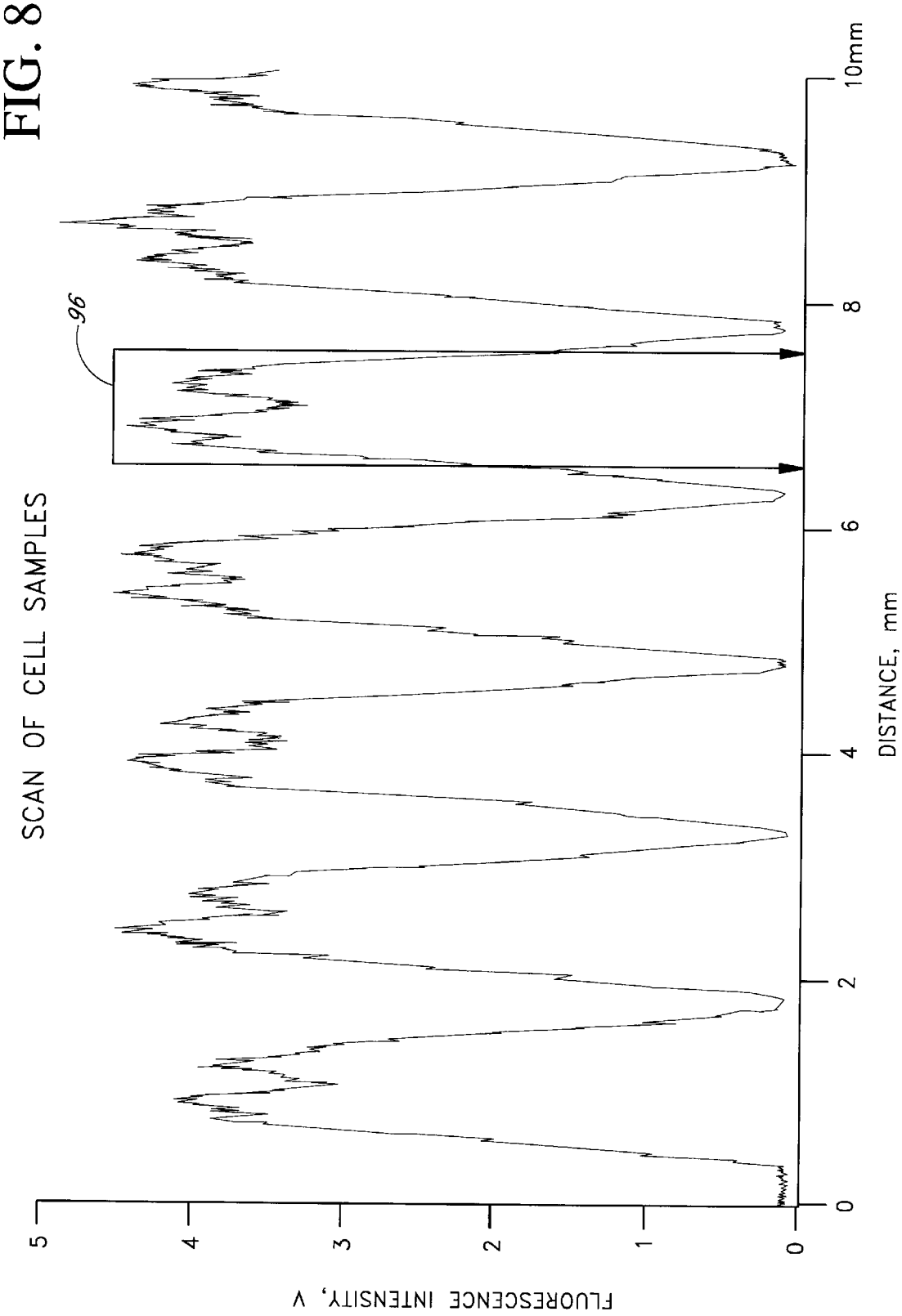
FIG. 8 is a plot of collected light intensity as a function of position during a scan of wells containing a fluorescent cell suspension.

Depending on the nature of the sample in the well, the peaks 88 may have different shapes. When liquid samples with dissolved fluorescent species are used, the peaks are nearly sinusoidal. As shown in FIG. 8, however, when cell samples are scanned, the peaks exhibit more complex internal structure.

To compute the fluorescence intensity for each well, an integration window 96 may be defined which partially encompasses the corresponding peak. This window should be small enough to avoid any cross-talk between adjacent wells but large enough to maximize the signal-to-noise ratio. The fluorescence intensity is then the sum average of all the data points enclosed inside this window. The window 96 is positioned with respect to the peak by sliding it back and forth until the resulting sum average is maximized. With this algorithm, the calculated fluorescence intensity is representative of the sample contained in the well even when a peak is not symmetrical, contains internal sub-peaks, etc. Thus, a high signal to noise ratio produces accurate measurements of fluorescence, while using a short time per sample well.

Figure 9:
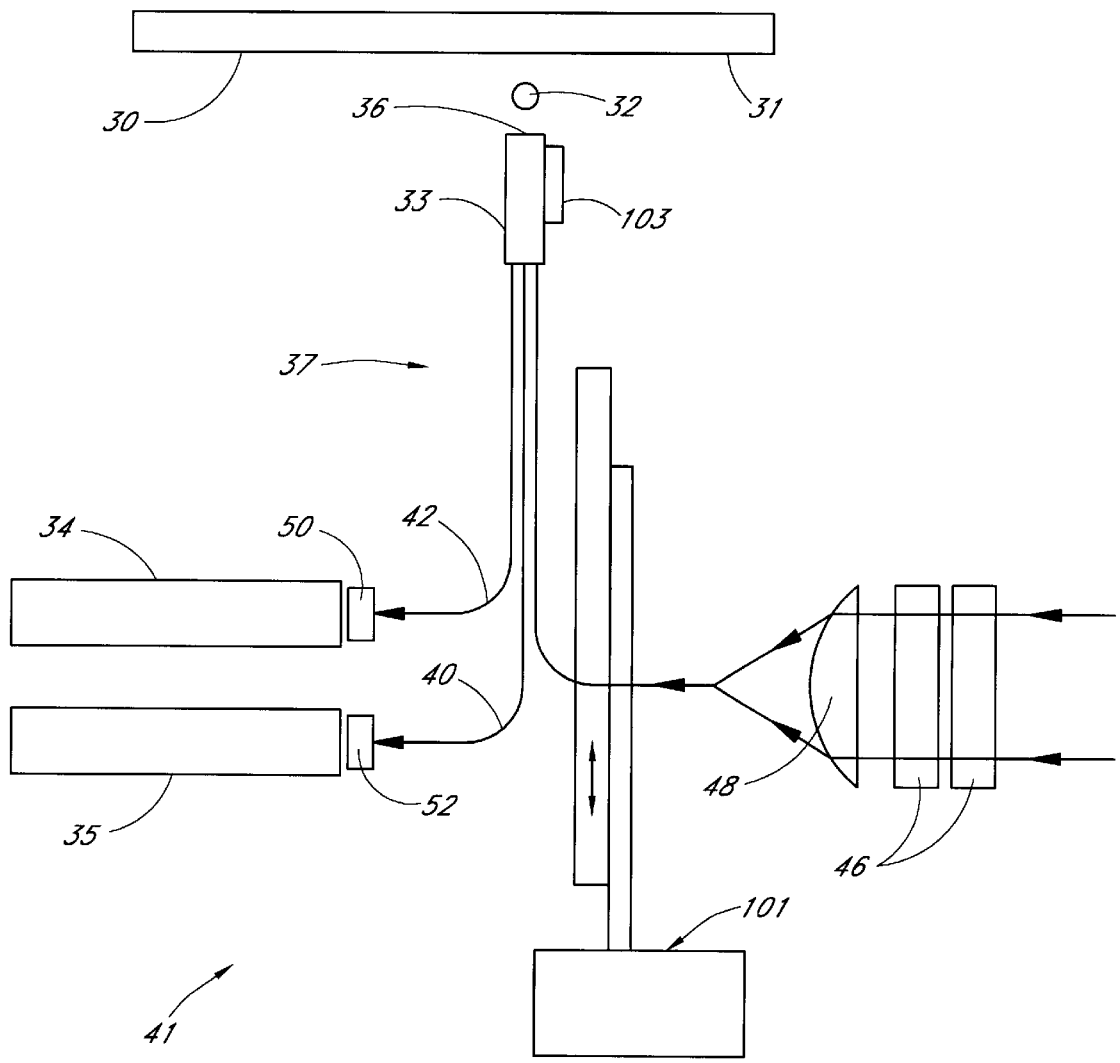
FIG. 9 is a schematic of another embodiment of a fluorescence excitation and emission detection system which may be part of the reaction module of the system of FIG. 1 or part of the reader of the system of FIG. 2.

In another aspect, the present invention comprises methods and apparatus to compensate for variations, inconsistencies and other differences in the dimensions, configuration and/or materials of the platform in which an assay is performed (e.g. a multiwell plate 30). Turning to FIG. 9, one such embodiment comprises methods and apparatus for adjusting the relative distance between the optics 37 of the light collector assembly 41 and the bottom surface 31 of the multiwell plate 30. The apparatus of FIG. 9 is similar to that of FIG. 3 and therefore elements common to both are not described again in detail here with respect to the description of the embodiment of FIG. 9. The adjustment feature may be used to compensate for the lack of flatness in the bottom surface 31 of the multiwell plate 30, other variations or inconsistencies in the bottom surface 31 or variations in different types and formats of multiwell plates.

The entire light collector assembly 41 is mounted on a vertical stage 101 oriented to provide adjustment in the vertical axis. The vertical stage 101 may be a motorized linear stage similar to the x, y stages described above. Alternatively, the plate positioner may be equipped with a motorized linear stage (not shown) to allow movement of the multiwell plate 30 in the vertical direction. A sensor 103 is provided on the light collector assembly 41 to measure the distance between the sensor 103 and the bottom surface 31 of the plate 30. A variety of sensing methods and apparatus suitable for use with the present invention for measuring the relative position of the bottom surface 31 and the optics 37 are known and are commercially available. In one embodiment, the sensor 103 is a Laser Displacement Sensor, Model LK-031, from Keyence. The Keyence sensor transmits a laser beam and measures the reflected light. Using a triangulation method, changes in the distance between the reflecting surface and the sensor are converted into an output signal that is proportional to the distance changes. In one embodiment, the nominal zero output distance between the sensor and the reflecting surface is about 30 mm, and the output signal varies at a rate of 1 volt per mm as this distance changes. The dynamic range of this particular sensor is about ±5 mm, and the resolution is about 1 $\mu$m.

Figure 10:
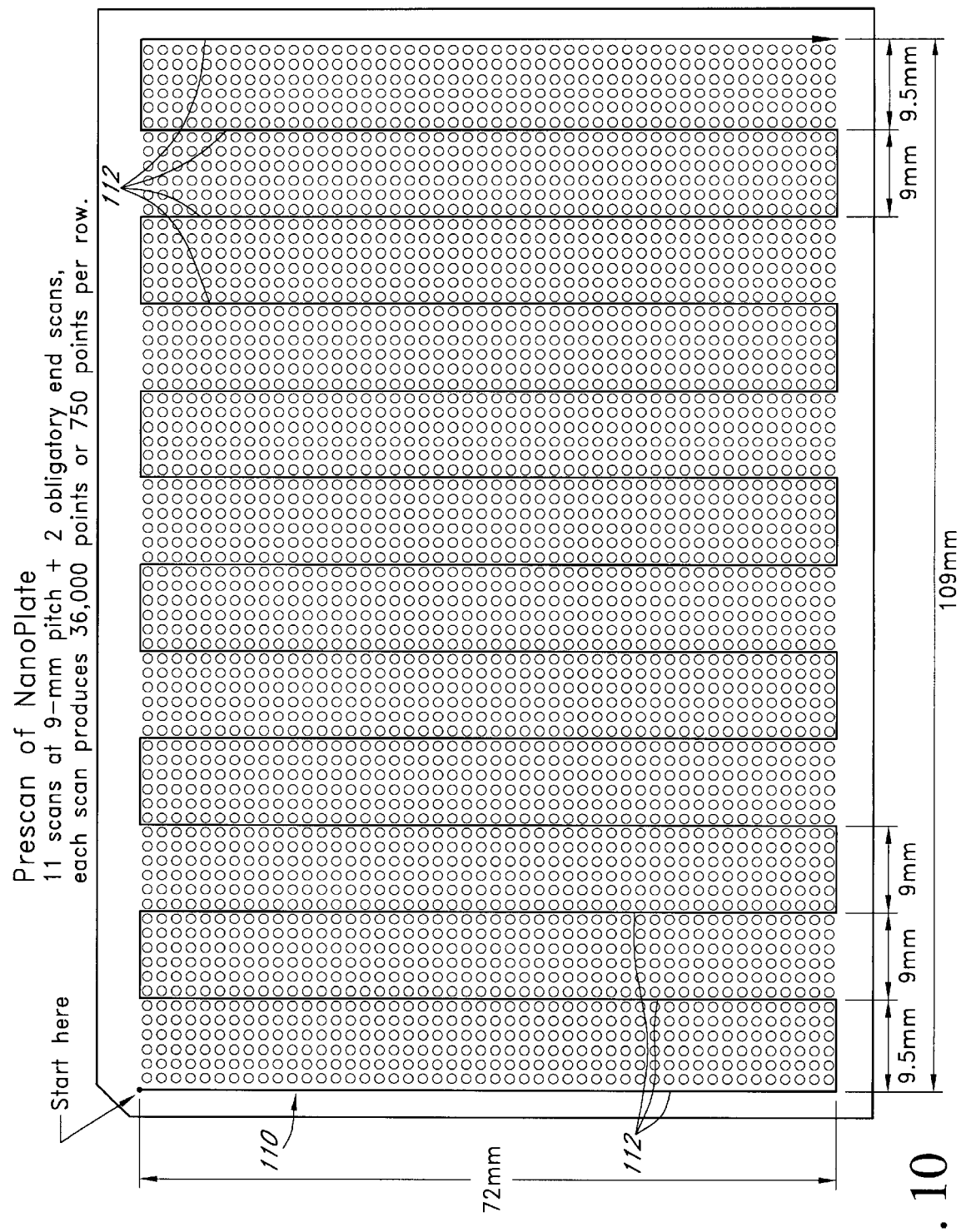
FIG. 10 is a diagram of one embodiment of a scanning pattern for mapping a bottom surface of a multiwell plate.

A first method of reading the plate 30 while compensating for variations in the elevation of the bottom surface 31 comprises first mapping the topology of the bottom surface 31 using a prescan of the bottom surface 31. The plate 30 is moved relative to the sensor 103 along all or a representative portion of the bottom surface 31. The plate may be moved in any desired pattern which covers the desired area, but is preferably moved in a raster scan. For example, FIG. 10 shows an exemplary prescan pattern 110 of a multiwell plate 30 having 48 rows of 72 wells each, for a total of 3456 wells in a rectangular pattern, and the dimensions as shown. High density multiwell plates, including a 3456-well plate, are disclosed in U.S. patent application Ser. No. 09/030,578, the disclosure of which is hereby incorporated herein by reference in its entirety. In this example, the scanning pattern 110 measures the elevation of the bottom surface 31 above the sensor 103 along the scan lines 112. The scan lines 112 are located between every sixth column and at each end of the plate 30 for a total of 13 scan lines with each scan line being 72 mm long. It should be understood that the scanning pattern could include more or fewer scan lines depending on the resolution desired. The scan lines 112 (except for the first and last) are preferably at the midpoint between the columns of wells. This is advantageous where the bottoms of the wells are transparent and may not reflect the laser beam of the sensor 103 sufficiently to obtain an accurate measurement.

Figure 11:
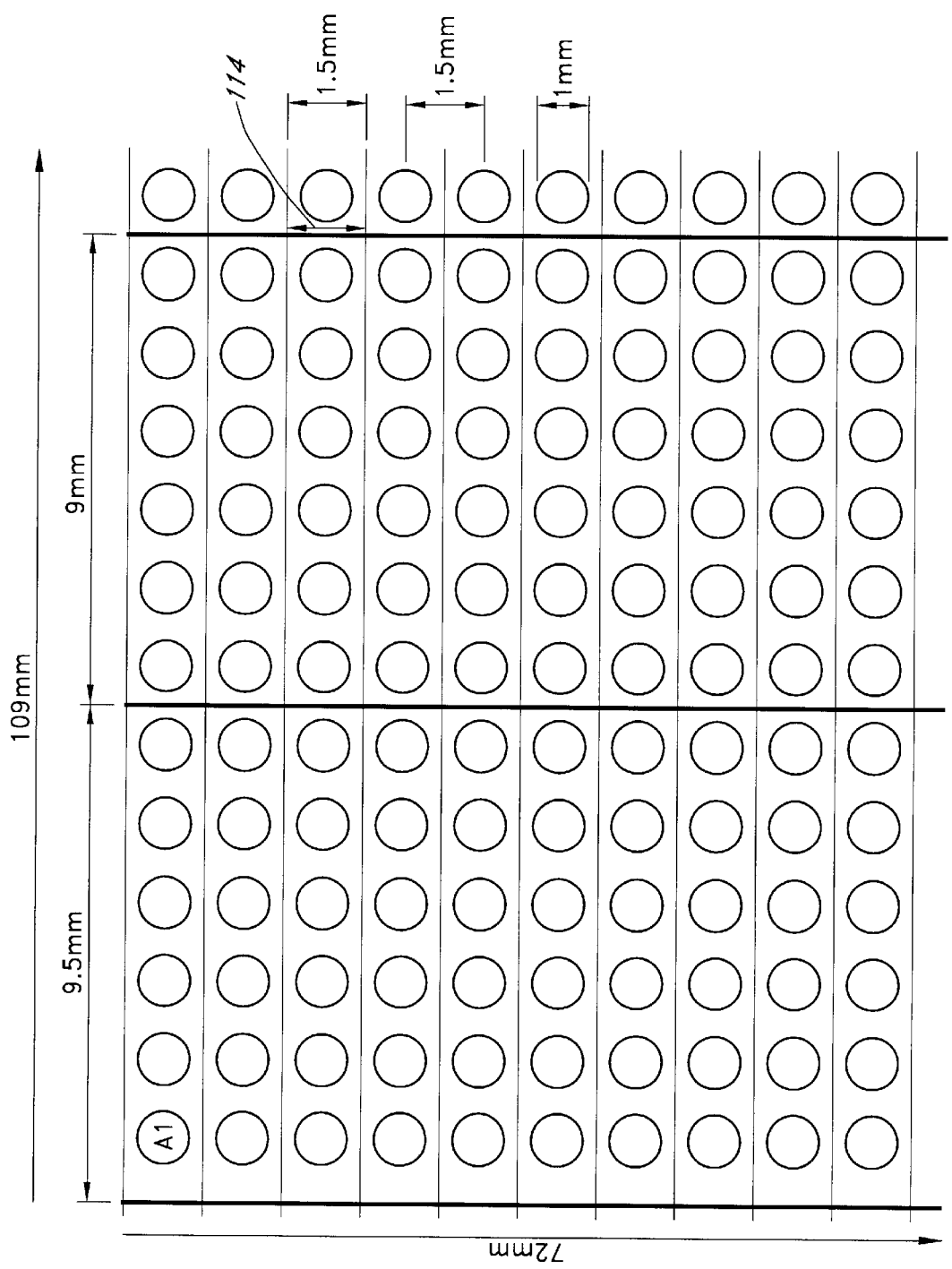
FIG. 11 is a partial enlarged view of the diagram of FIG. 10.
Figure 12:
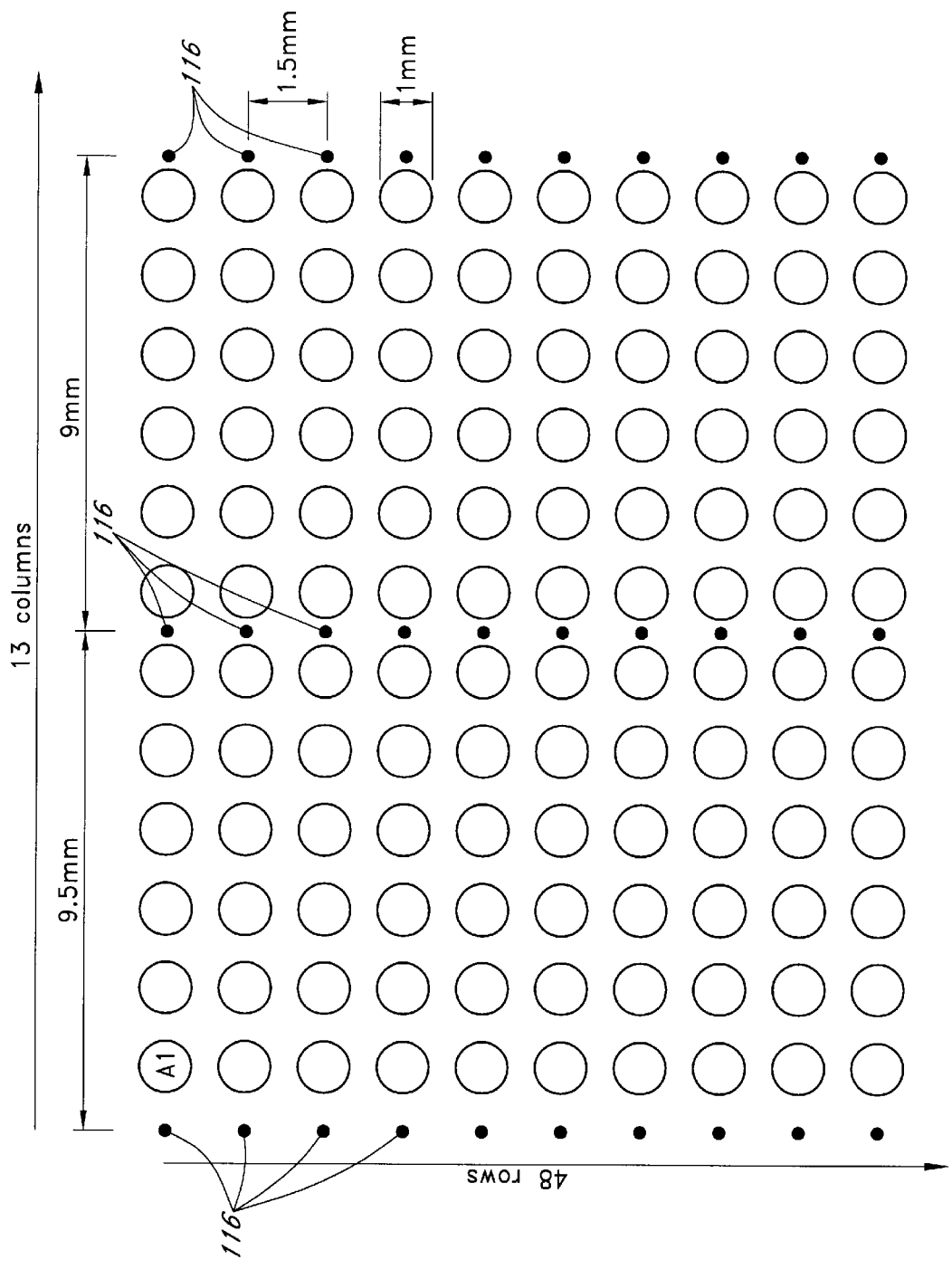
FIG. 12 is another partial enlarged view of the diagram of FIG. 10.

As the plate is moved along the scanning pattern 112, the sensor 103 measures the elevation of the bottom surface 31 at the location of the sensor 103. Referring to FIG. 11, each scan line 112 can be broken down into forty-eight 1.5 mm segments 114 where each such segment symmetrically straddles a well. The analog output of the Keyence sensor 103 is digitized using the same position-based acquisition method described above for obtaining fluorescence data in the wells of a multiwell plate. Each 72-mm scan line 112 results in a number of sample points. In the case of data acquisition about every 2 $\mu$m, about 36,000 sample points are obtained. Or breaking it down per well, each of the 48 segments 114 adjacent each well in a scan line 112 has 750 sample points. The sample points for each well are averaged and these 48 averages represent the elevation of 48 points 116 on the bottom surface 31. The points 116 on the bottom surface 31 are shown schematically in FIG. 12. Of course, a higher or lower level of sampling and density of elevation measurements may be used depending on the accuracy and speed required. Indeed, a single measurement could be taken at each of the points depicted in FIG. 3. However, the high level of oversampling and averaging used in this example reduces imprecise measurements that may be due to random imperfections in the bottom surface 31.

Figure 13:
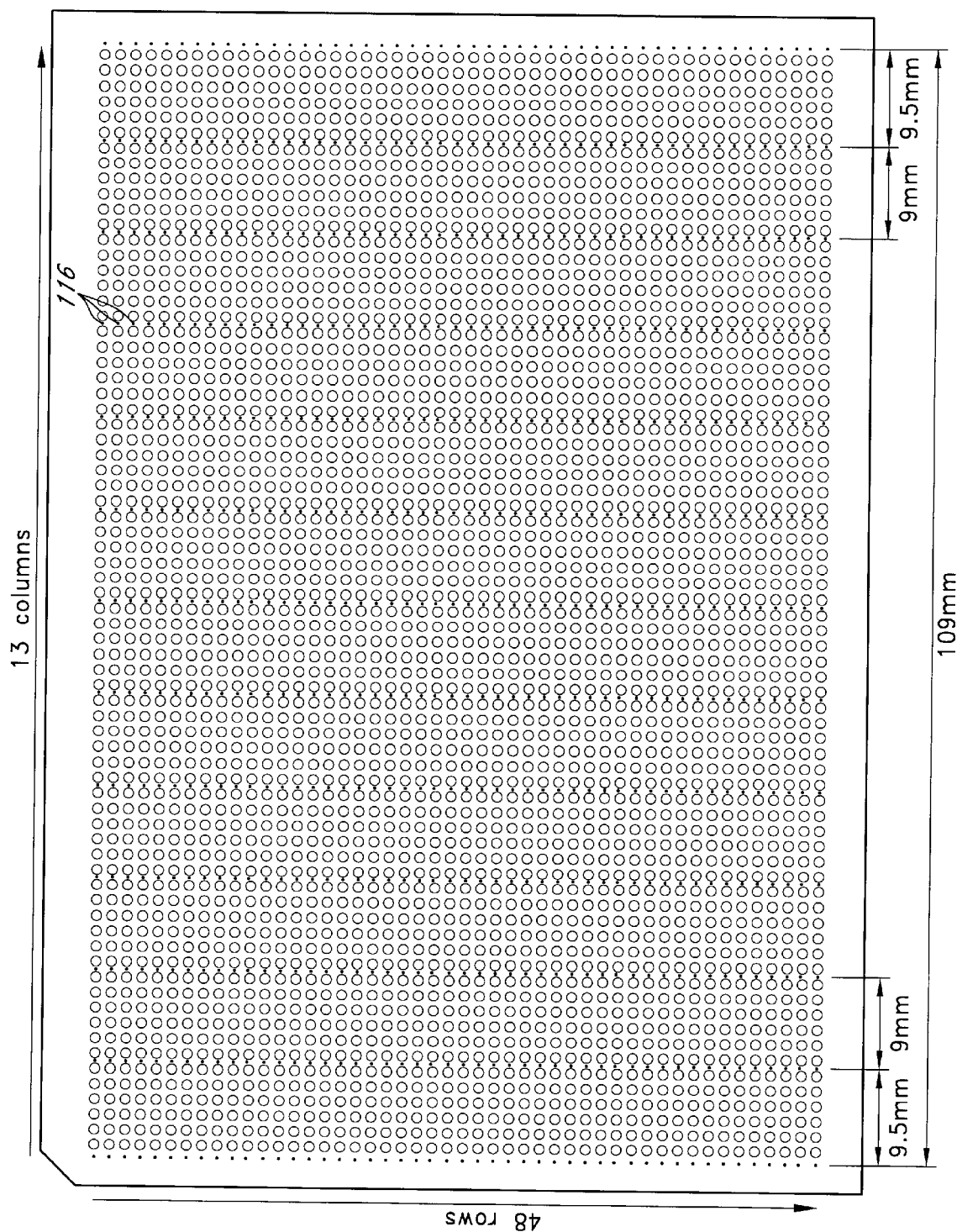
FIG. 13 is a diagram of a multiwell plate with a matrix of elevation points on the bottom surface of the multiwell plate.
Figure 14:
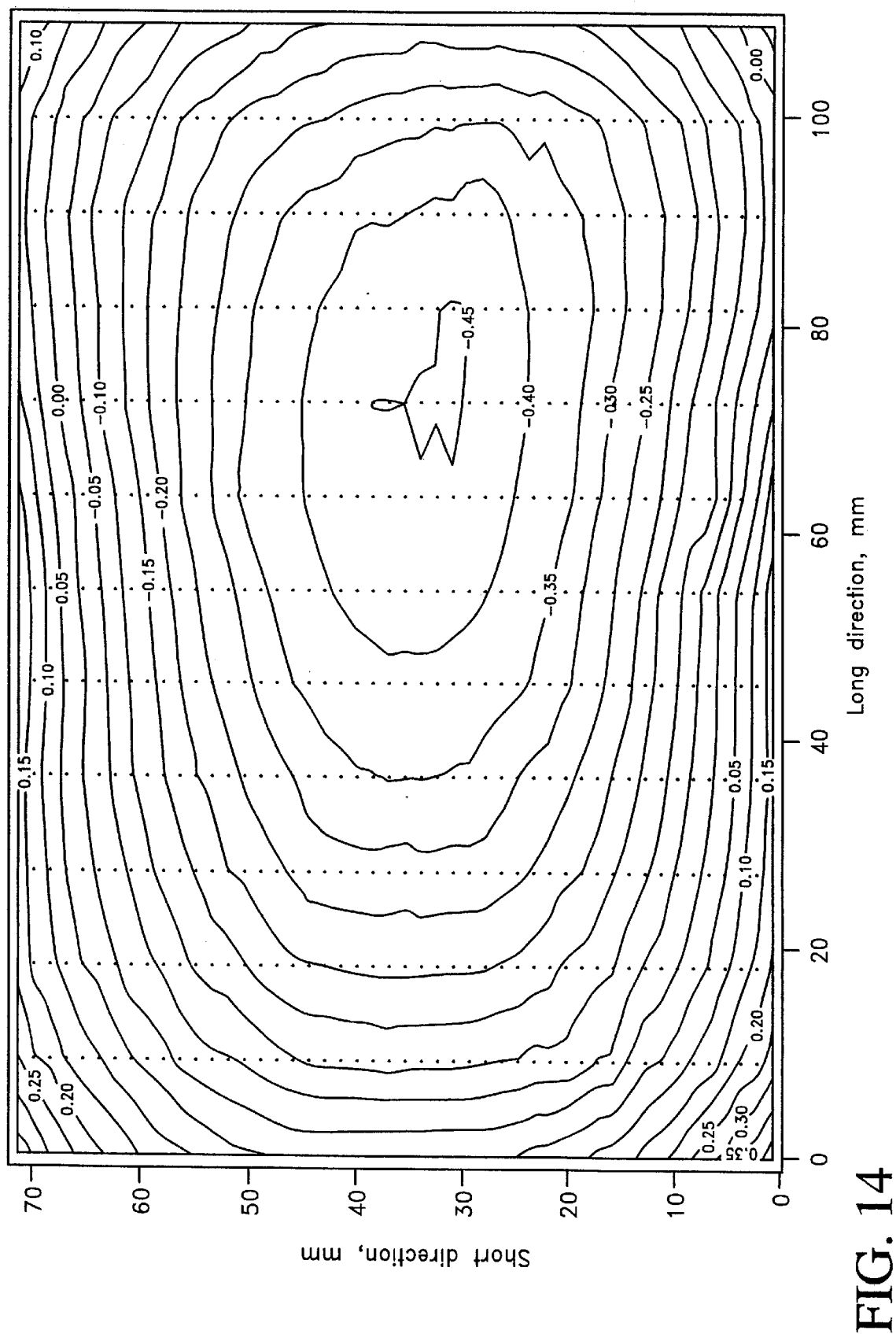
FIG. 14 is an exemplary contour map of the bottom surface of a multiwell plate.

The elevation measurement and averaging method results in a 48×13 matrix of elevation points as shown in FIG. 13. The elevation matrix represents a topological map of the bottom surface 31. In fact, a contour map of the elevation points 116 can be constructed as shown in the example of FIG. 14. In this example, it can be seen that the bottom surface 31 has a generally elongated valley roughly centered in the short direction and slightly shifted to the right in the long direction. The difference in elevation from the lowest point at the bottom of the valley to the highest point on the lower left hand corner is about 0.6 mm in this example.

Figure 15:
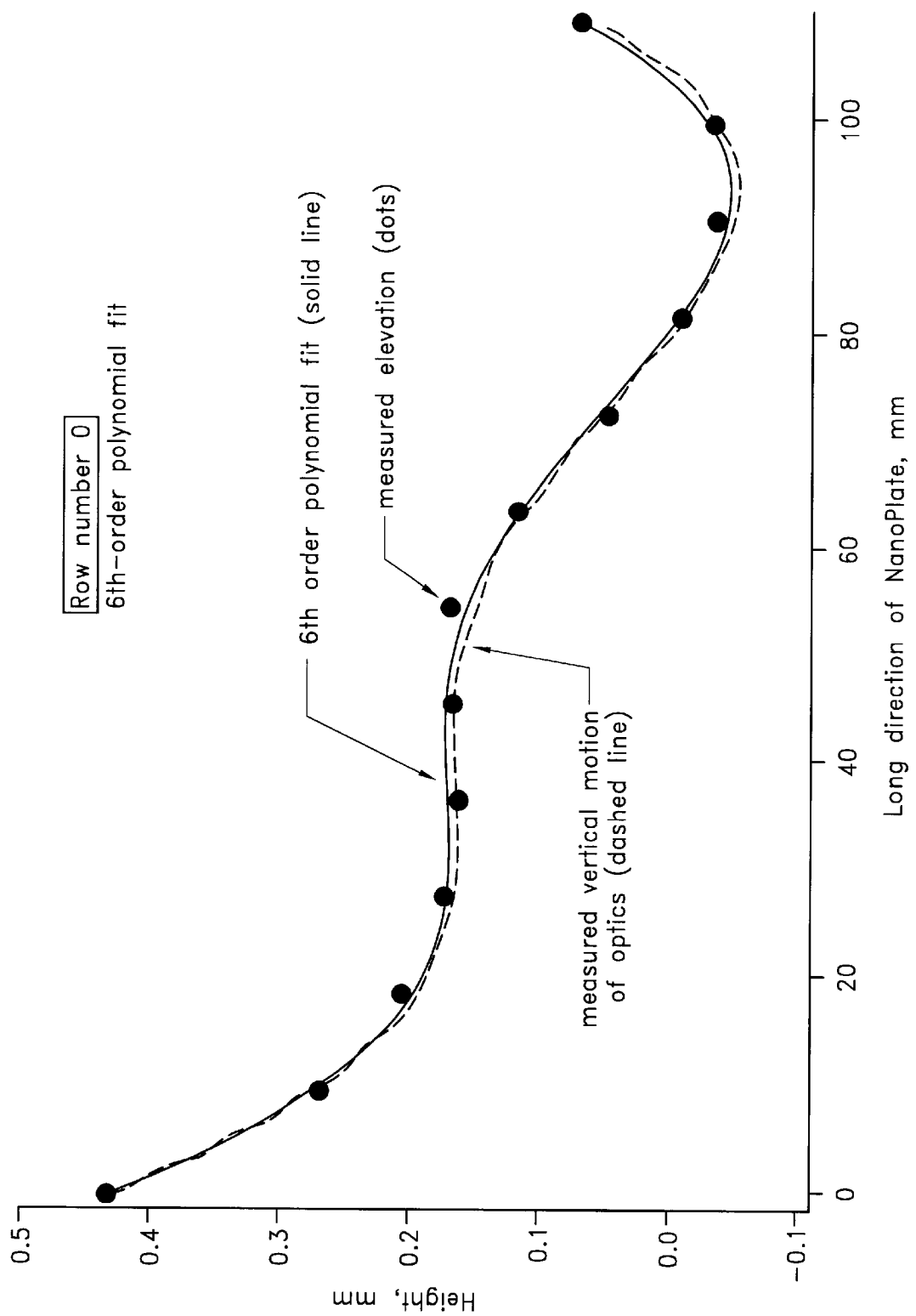
FIG. 15 is a plot of an exemplary 6-th order polynomical fit of the elevation of the bottom surface along row 0 of a multiwell plate.
Figure 16:
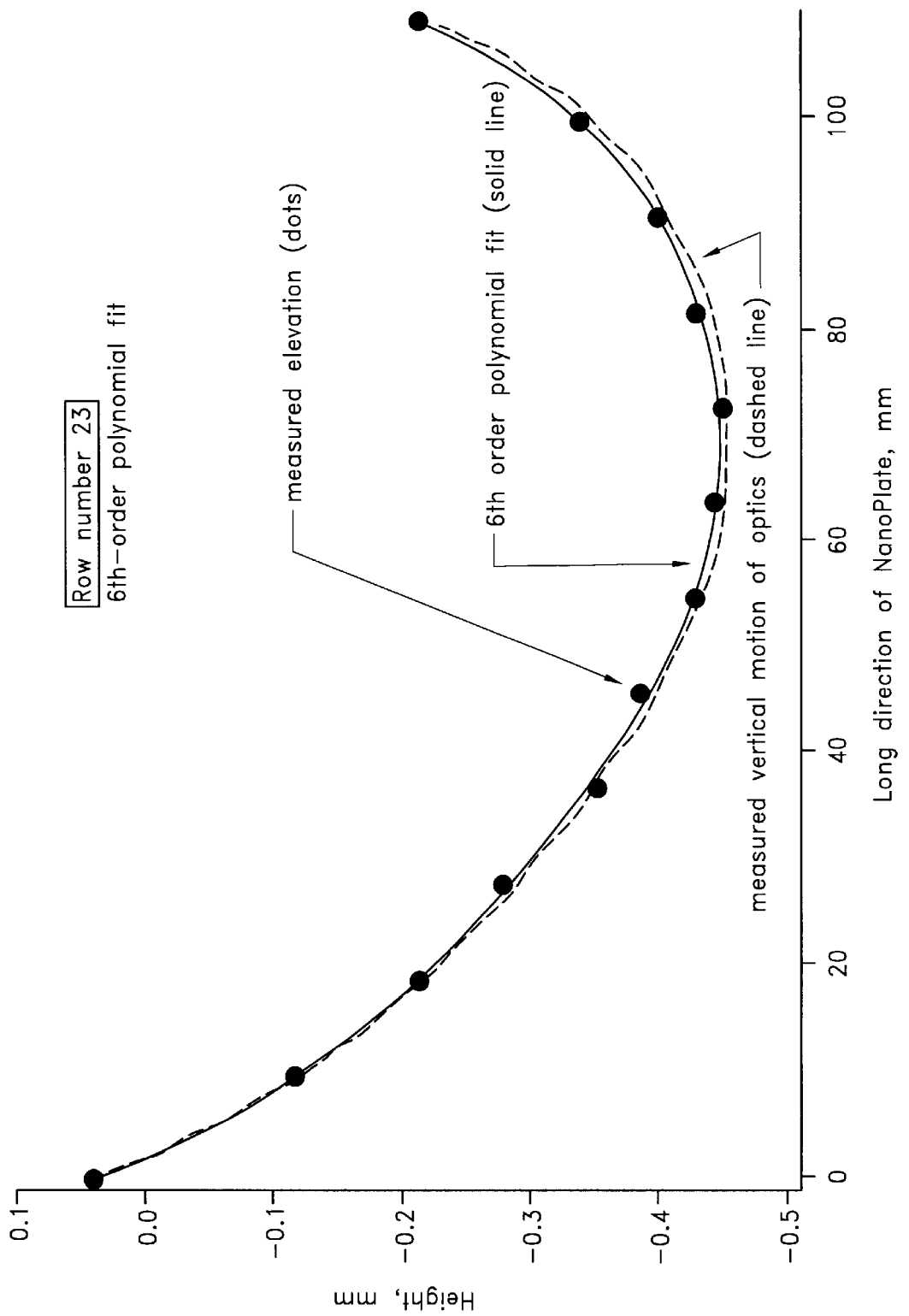
FIG. 16 is a plot of an exemplary 6-th order polynomical fit of the elevation of the bottom surface along row 23 of a multiwell plate.
Figure 17:
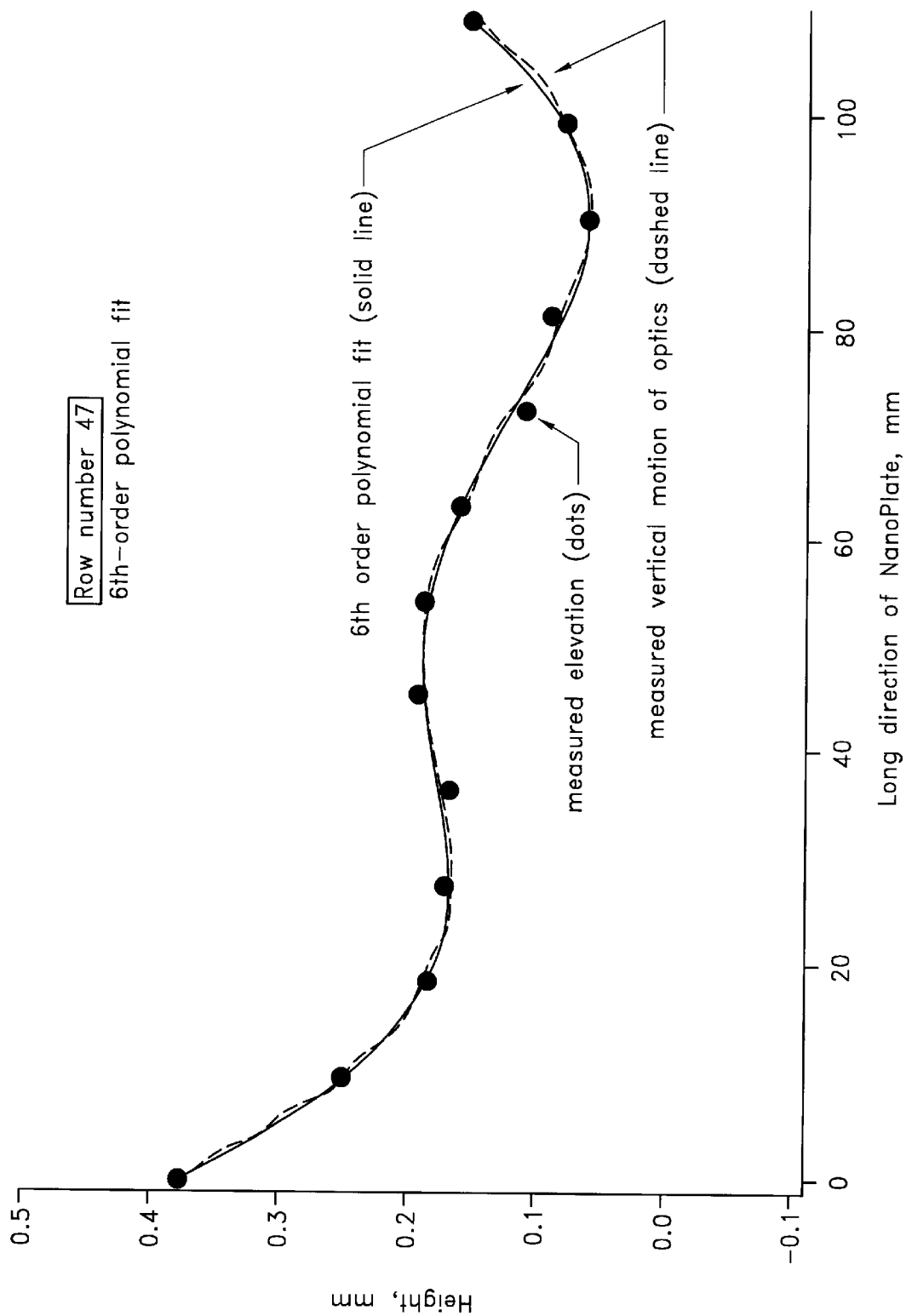
FIG. 17 is a plot of an exemplary 6-th order polynomical fit of the elevation of the bottom surface along row 47 of a multiwell plate

While the contour map may be informative, it is advantageous to compute position profiles along scan lines. Referring back to FIG. 2, in one embodiment, sequential scans are performed down each of the 48 rows of wells during the plate reading process. Thus, to perform the scan of each well row while compensating for elevation changes in the bottom surface, the thirteen data points gathered along each well row may be fit to curves which smoothly approximate the bottom surface contour along each row. The 48 profiles may advantageously be computed from the 48 rows of the elevation matrix by fitting each set of thirteen points to a polynomial function of bottom surface height as a function of position along the row. In one embodiment, a fit to a $6^{th}$-order polynomial is made. For this example, the fits to rows 0, 23 and 47 of the plate contour illustrated in FIG. 14 are shown in FIGS. 15, 16 and 17, respectively, with the difference in height from an approximately 30 mm nominal height above the sensor (defined by a flat reference plate during a calibration procedure as described in additional detail below) plotted on the vertical axis and the distance along each row plotted along the horizontal axis. The smooth curves in FIGS. 15–17 thus represent the approximate trajectories that the optics 37 should follow as the bottom surface 31 of the plate passes over it during a scan of each respective row.

Figure 18:
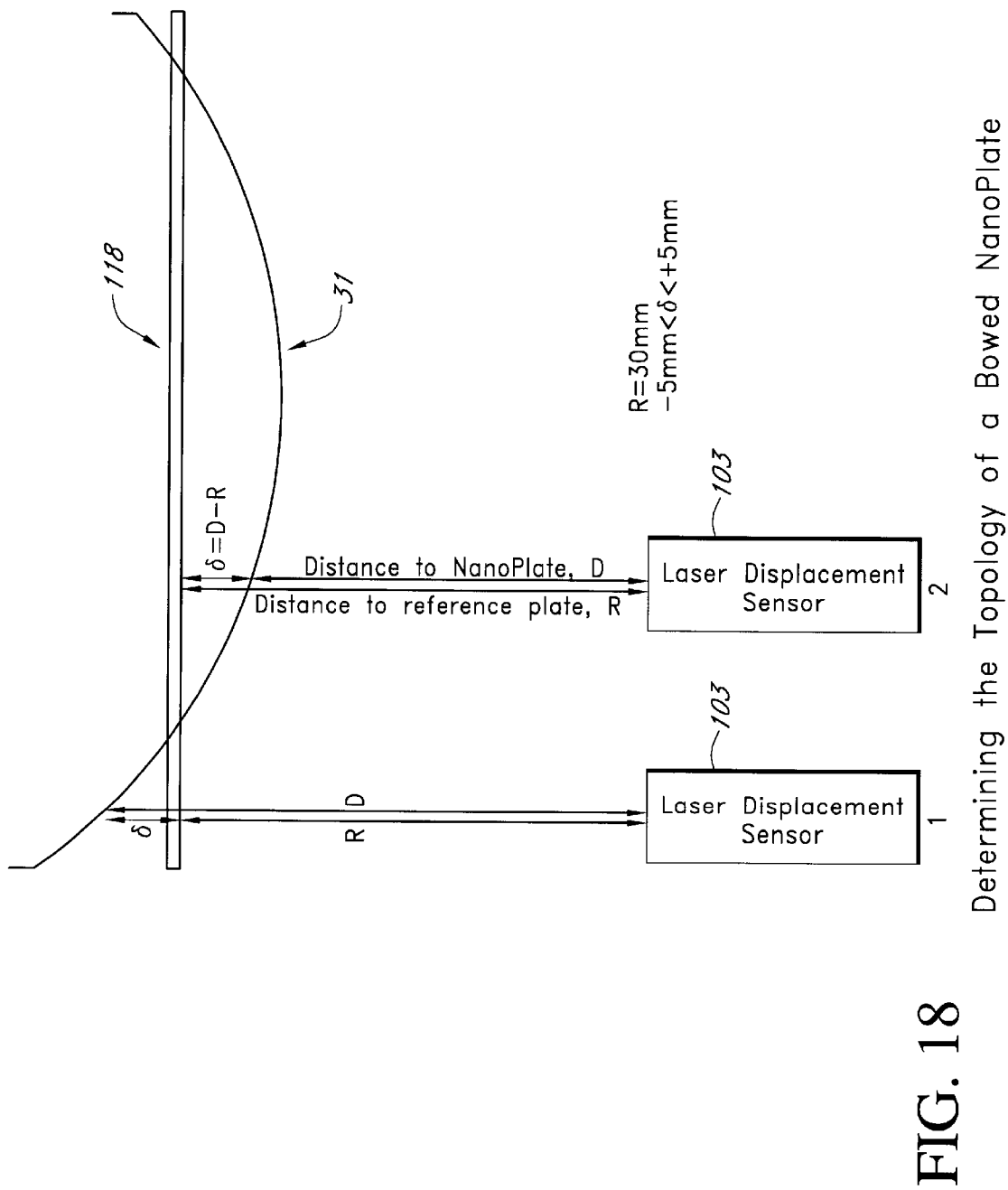
FIG. 18 is a diagram of a system for calibrating a detection system according to the present invention.
Figure 19:
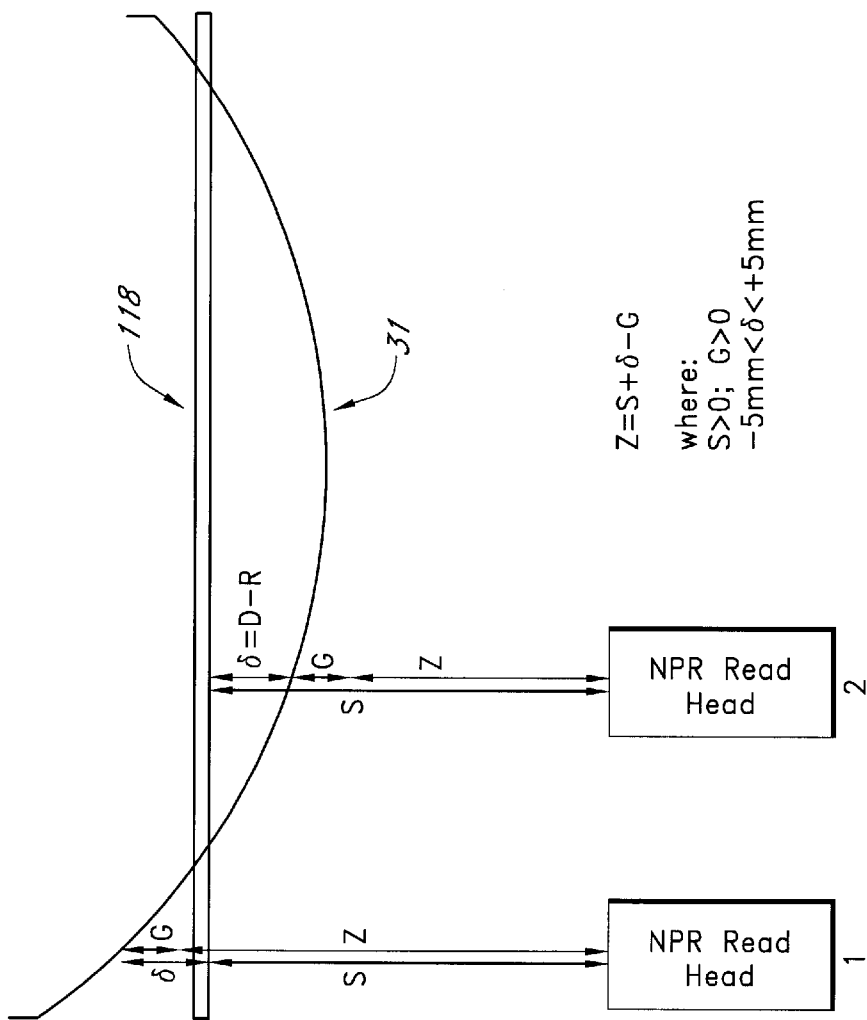
FIG. 19 is another diagram of a system for calibrating a detection system according to the present invention.

The profiles computed above relate to the distance between the bottom surface 31 and the sensor 103. These profiles are preferably transformed to an absolute vertical distance "Z" that the optics 37 must be moved from an initial home or rest position as a function of plate position over the course of the scan of a row to maintain a constant pre-selected gap "G" between the optics and the bottom surface of the multi-well plate. Turning to FIGS. 18 and 19, one method to accomplish this is to calibrate the scanner by placing a flat reference plate 118 into the plate positioner instead of a multiwell plate.

To calibrate the scanner with the reference plate, the absolute distance S between the home or rest position of the optics 37 and the bottom of the reference plate 118 is measured. This may be done by raising the light collector assembly with the vertical stage 101 from the home position until the optics 37 barely touches the reference plate and measuring the distance traveled (S), with, for example, a position encoder provided as part of the vertical stage. In addition, the elevation of the reference plate 118 is measured using the sensor 103 in the same or similar scanning and averaging method described for measuring the elevation of the bottom surface 31 of the multi-well plate. The distance R between the sensor and the reference plate 118 may be computed as the average of the reference plate's 48×13 elevation matrix. To determine the correct absolute distance Z from the home position that the vertical stage should be from the home position as a row passes over it, the row profile functions are corrected with the measurement from the reference plate 118. Specifically, the distance Z is given by:

$$Z = S + \delta - G$$

where S is the measured distance to make the optics touch the reference plate, G is the desired gap, and $\delta$ is the difference between the reference plate measurement and the measurement profiles produced when measuring the bottom of the multi-well plate. The row contour profiles are thus zeroed around the position of the bottom surface of the reference plate 118, and the vertical position corrections made during a scan are made with reference to the known measured absolute distance S between the top of the optics and the bottom of the reference plate 118.

Figure 20:
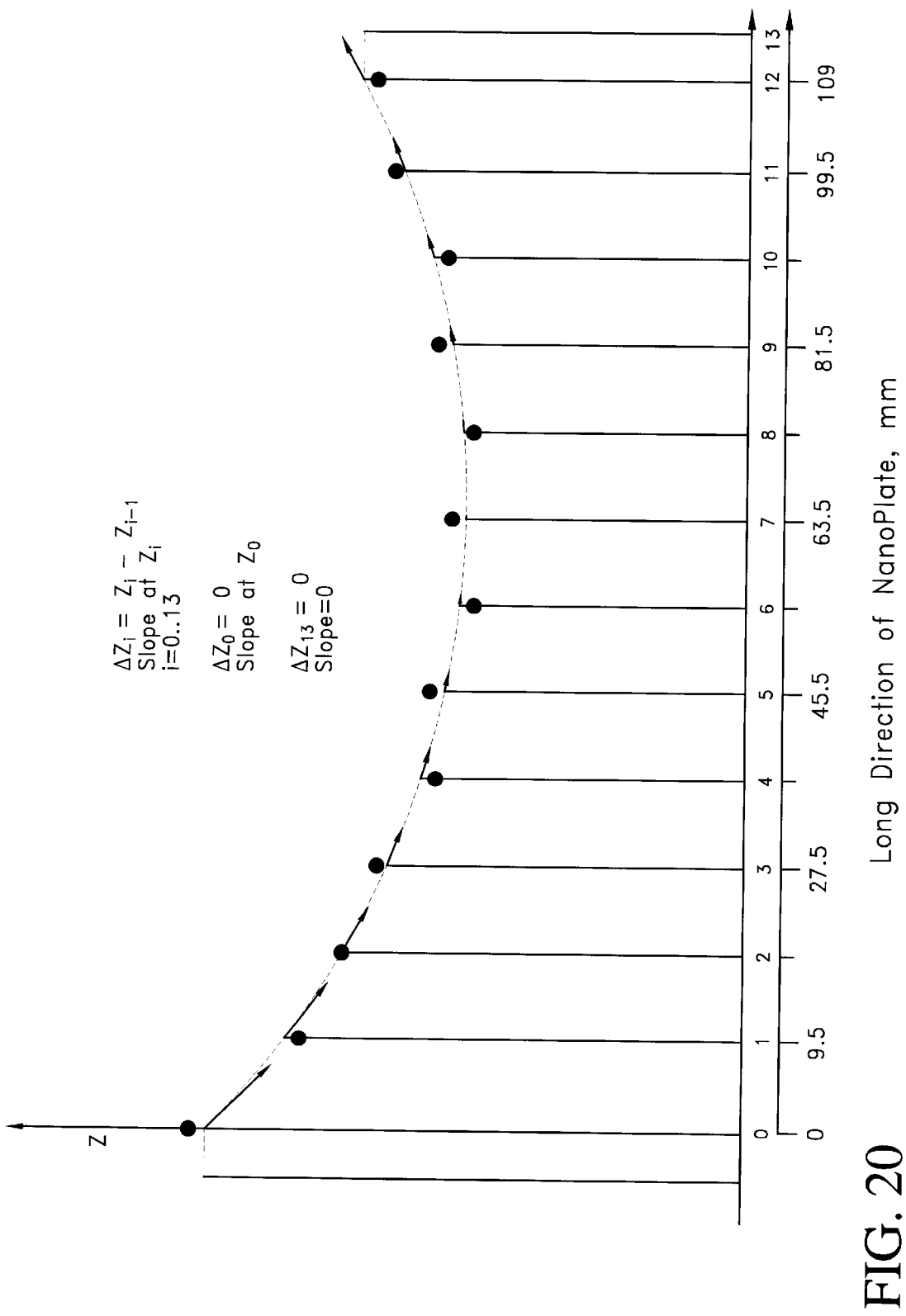
FIG. 20 is a plot of profile data representing the amount of vertical adjustment of the optics of a detector along a scan line of a multiwell plate.

Once the profiles of the vertical adjustment of the optics 37 for the scan of each row of wells has been determined, information defining the profiles may be loaded into a controller that controls the plate positioning stages and the vertical stage. High accuracy position control can be performed in a variety of ways, and several different products are commercially available which are suitable for use with the present invention. In one simple embodiment, the correct Z displacement at each well position can be estimated from the calculated curves such as those illustrated in FIGS. 15–17, and the vertical position of the optics can be appropriately adjusted during a dwell time adjacent to each well. In another advantageous embodiment, the height corrections are performed in small steps as the optics continuously scans the length of each row. For the latter embodiment, it has been found suitable to control the stages with a model 6K4 motion controller from the Compumotor division of Parker Controls. Referring now to FIG. 20, when the above mentioned model 6K4 controller is used, the amount of data downloaded to the controller to define the path the optics should follow can be minimized by defining the profile along each well row with a series of segments, with each segment being in turn defined by (1) an amount of horizontal travel of the plate positioning stage, (2) an amount of vertical travel of the vertical stage, and (3) a segment slope. The appropriate values for each segment may be obtained from the polynomial fits to the 48 profiles (see FIGS. 15–17). For the i-th segment, the vertical travel $\Delta Z_i$ is computed as $Z_i - Z_j$. The slope for the beginning of the i-th segment is the slope at the end point of the previous segment. Two additional segments called lead-in and lead-out are added at the beginning and end of the profile, respectively. The lead-in and lead-out segments are 0.5 mm long horizontally and both have a vertical travel $\Delta Z$ of zero. The slope for the lead in segment is the initial profile slope at $Z_0$. For the lead-out segment, the slope is zero. With this downloaded information, the 6K4 controller calculates motion criteria such as acceleration, speed and distance needed to substantially track the profiles for the scan of each row.

The scan of each row of 72 wells may therefore proceed as follows. The plate is positioned at the starting point adjacent the center of the first well. The optics 37 are moved a distance $Z_0$ up from the home position by the vertical stage 101 in accordance with the desired gap G and the multi-well plate/reference plate calibration measurements described above. The plate is then scanned along its long direction to the end of the row. During this scan, the optics 37 are moved up and/or down according to the profile to maintain a substantially constant distance between the optics 37 and the bottom surface 31 along the first row. This process is repeated for each of the 48 rows of the 3456-well plate 30.

Using the described method and apparatus and a second sensor (not shown) provided to monitor the height of the optics 37, it can be shown empirically that the vertical position of the optics 37 may be successfully adjusted to compensate for the varying elevation of the bottom surface 31 of the plate 30. In this example, the same plate 30 used as an example above for the map of FIG. 14 and the calculated profiles of rows 0, 23 and 47 as shown in FIG. 15–17, respectively, was used. A second sensor was used to measure the height of the optics 37 as the plate 30 was scanned using the profiles obtained as described above. The data from the monitoring sensor was then superimposed on the fitted profiles for each row. The results for rows 0, 23, and 47 are shown in FIGS. 15, 16 and 17, respectively. It can be seen that the actual motion of the optics 37 closely matches the desired profiles.

Figure 21:
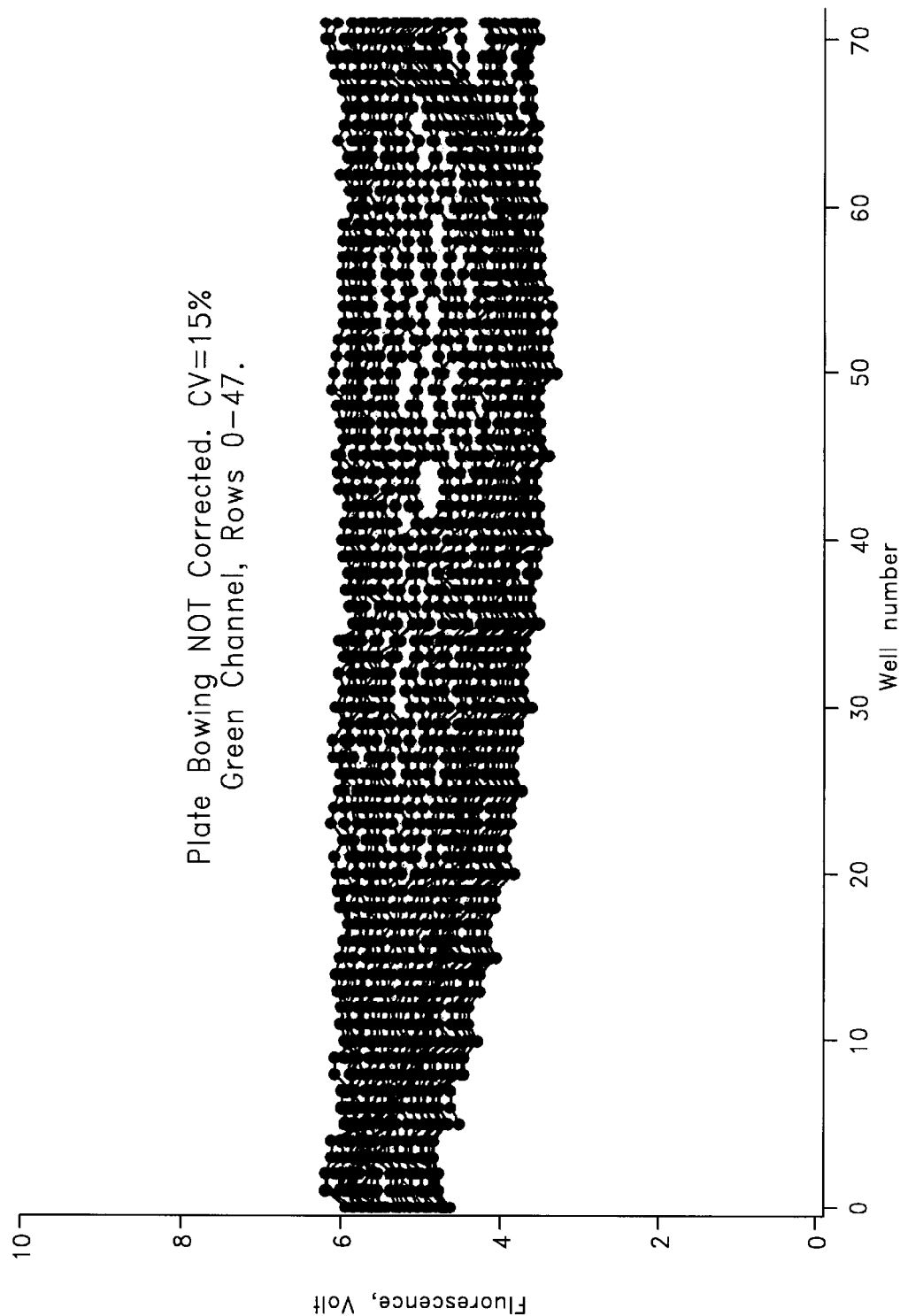
FIG. 21 is a plot of collected light intensity for a scan of all 72 wells of each of the 48 rows of a 3456-well plate with the optics vertical profiling deactivated.
Figure 22:
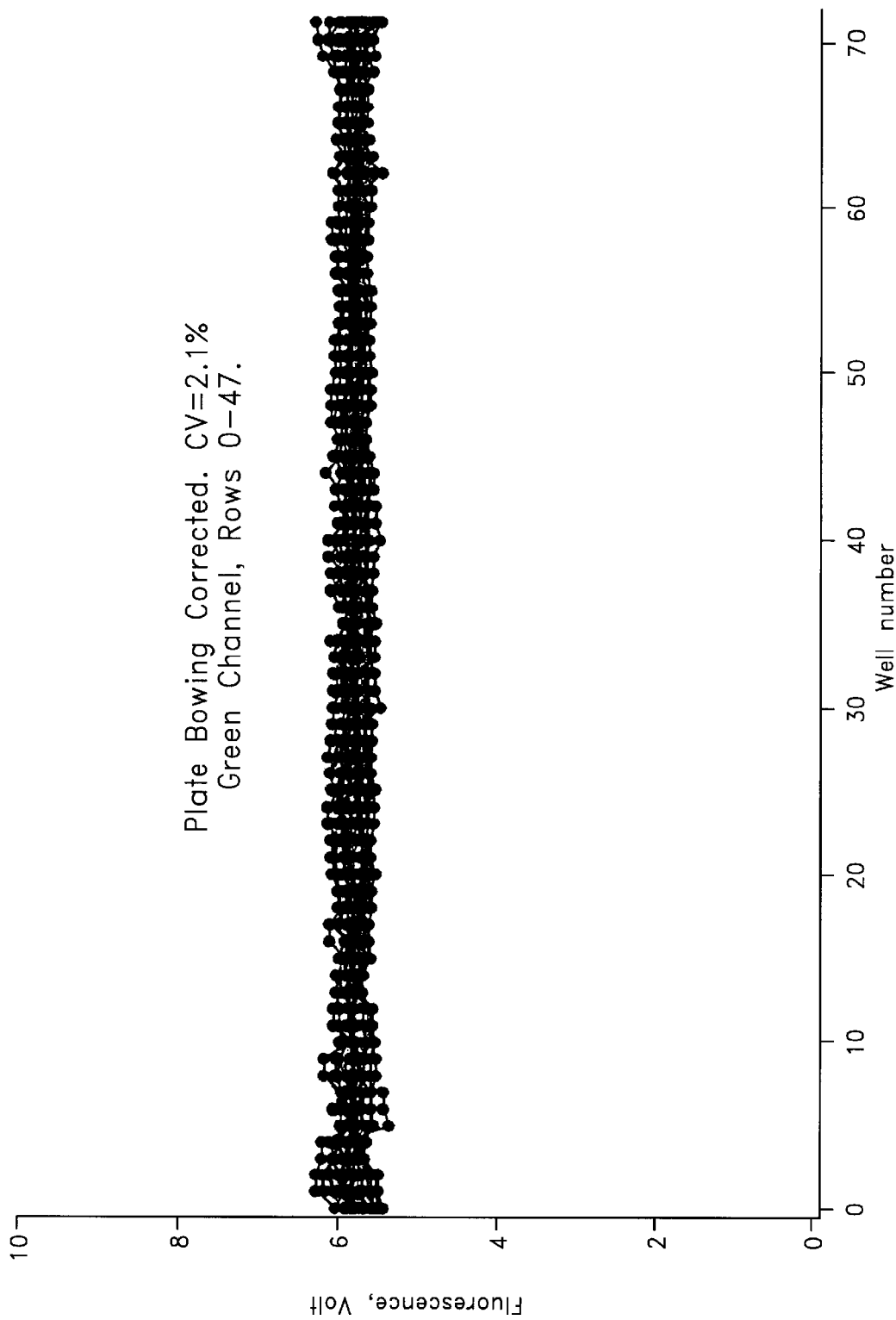
FIG. 22 is a plot of collected light intensity for a scan of all 72 wells of each of the 48 rows of a 3456-well plate with the optics vertical profiling activated.
Figure 23:
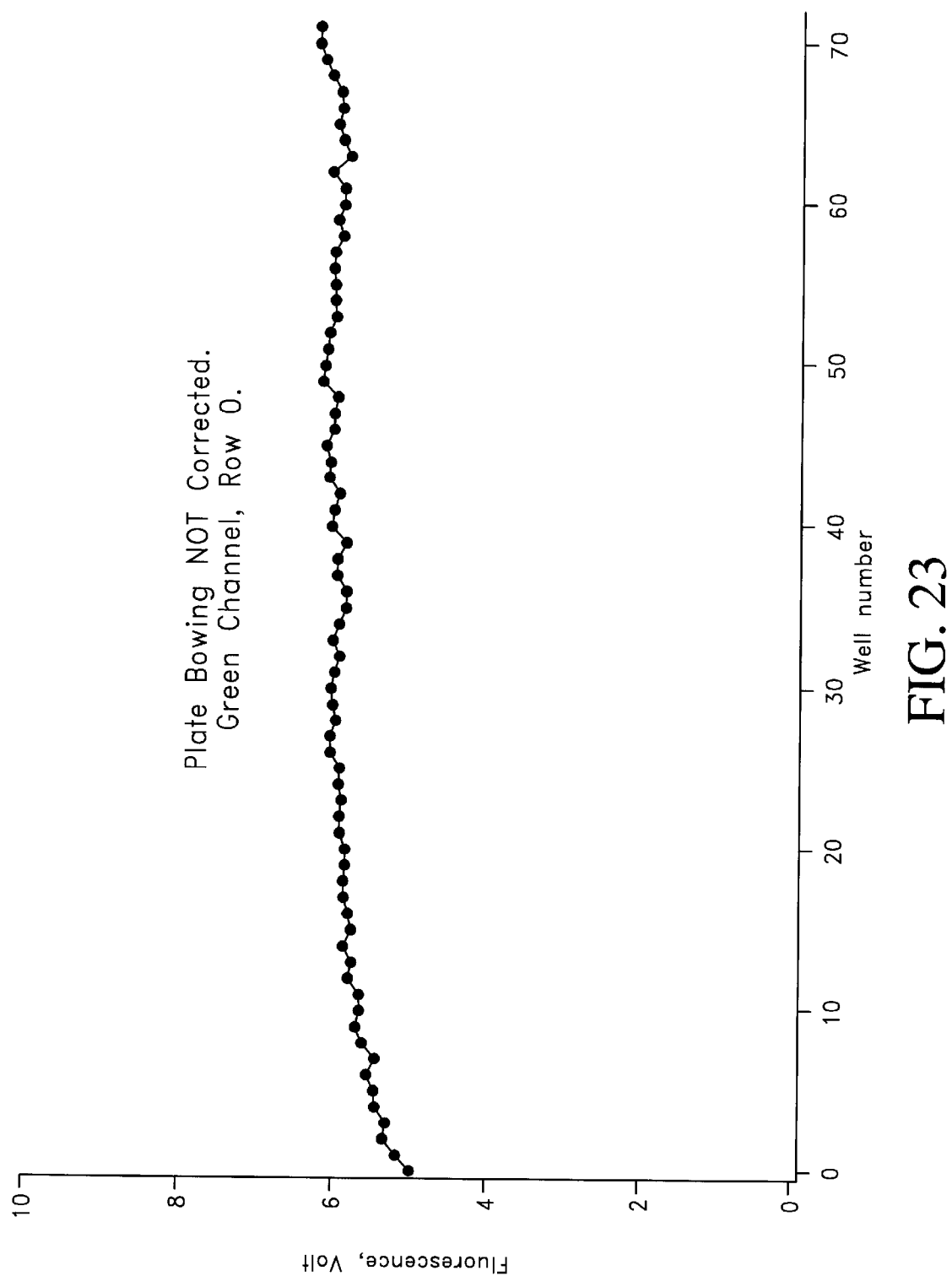
FIG. 23 is a plot of collected light intensity for a scan of all 72 wells of row 0 of a 3456-well plate with the optics vertical profiling deactivated.
Figure 24:
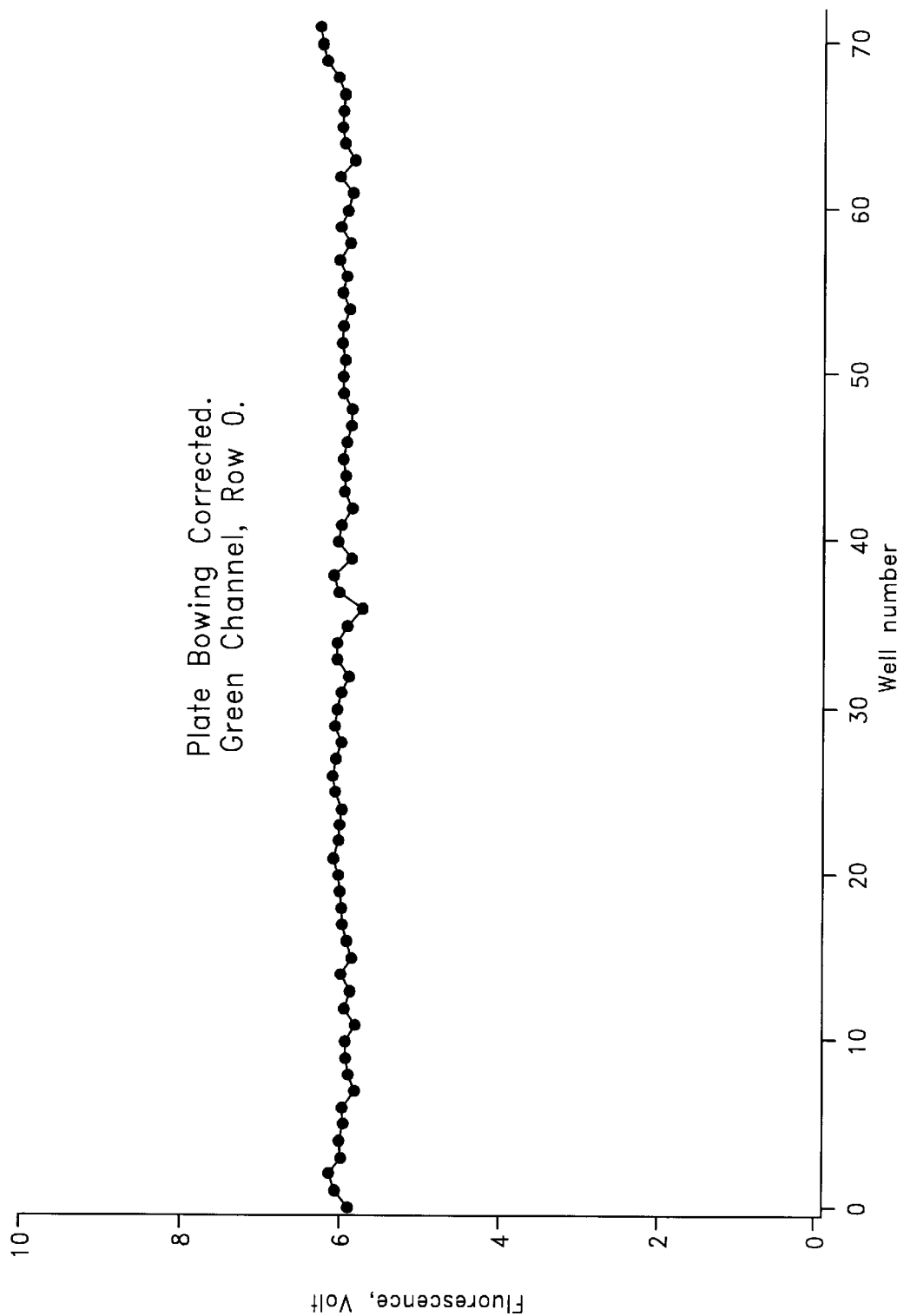
FIG. 24 is a plot of collected light intensity for a scan of all 72 wells of row 0 of a 3456-well plate with the optics vertical profiling activated.
Figure 25:
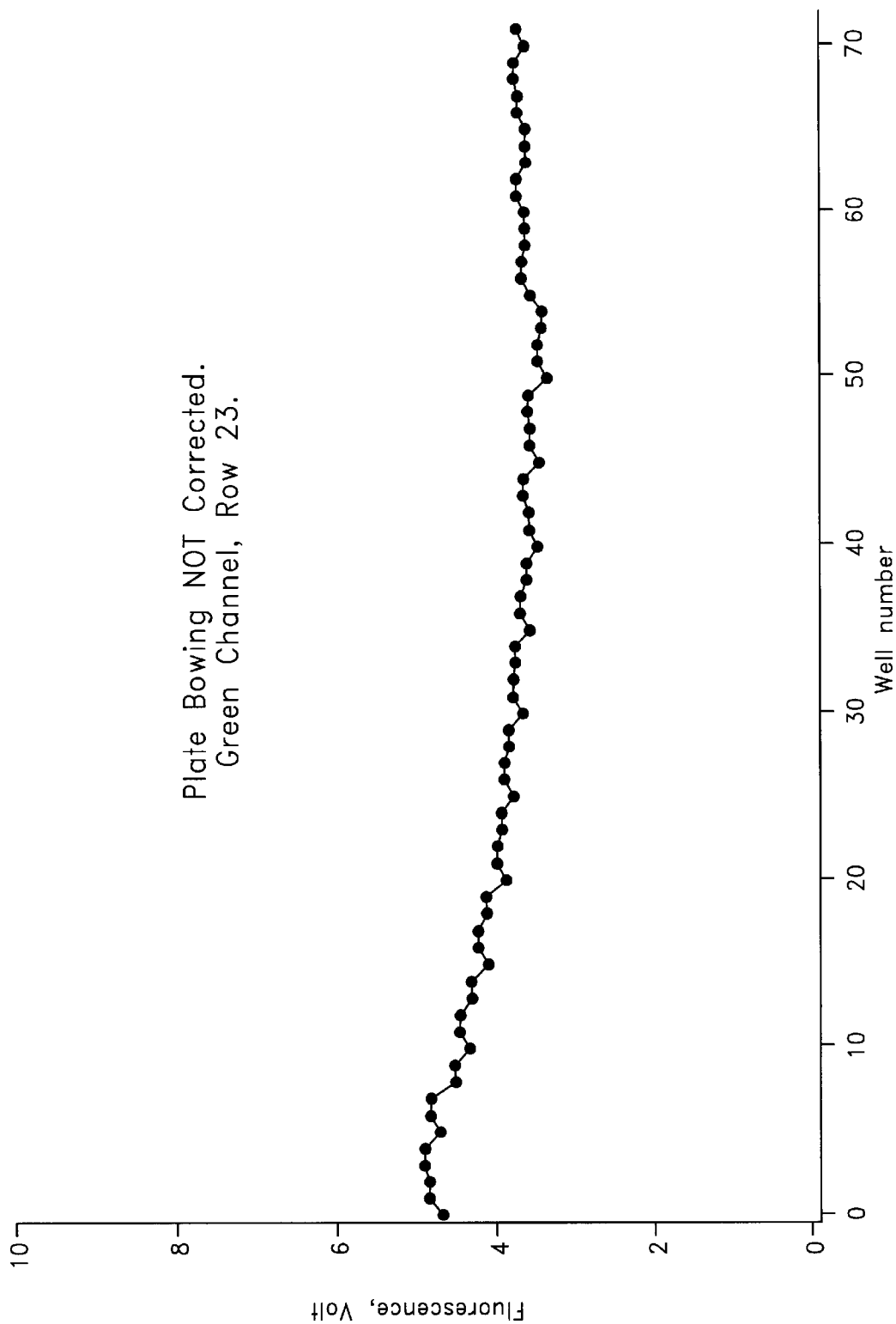
FIG. 25 is a plot of collected light intensity for a scan of all 72 wells of row 23 of a 3456-well plate with the optics vertical profiling deactivated.
Figure 26:
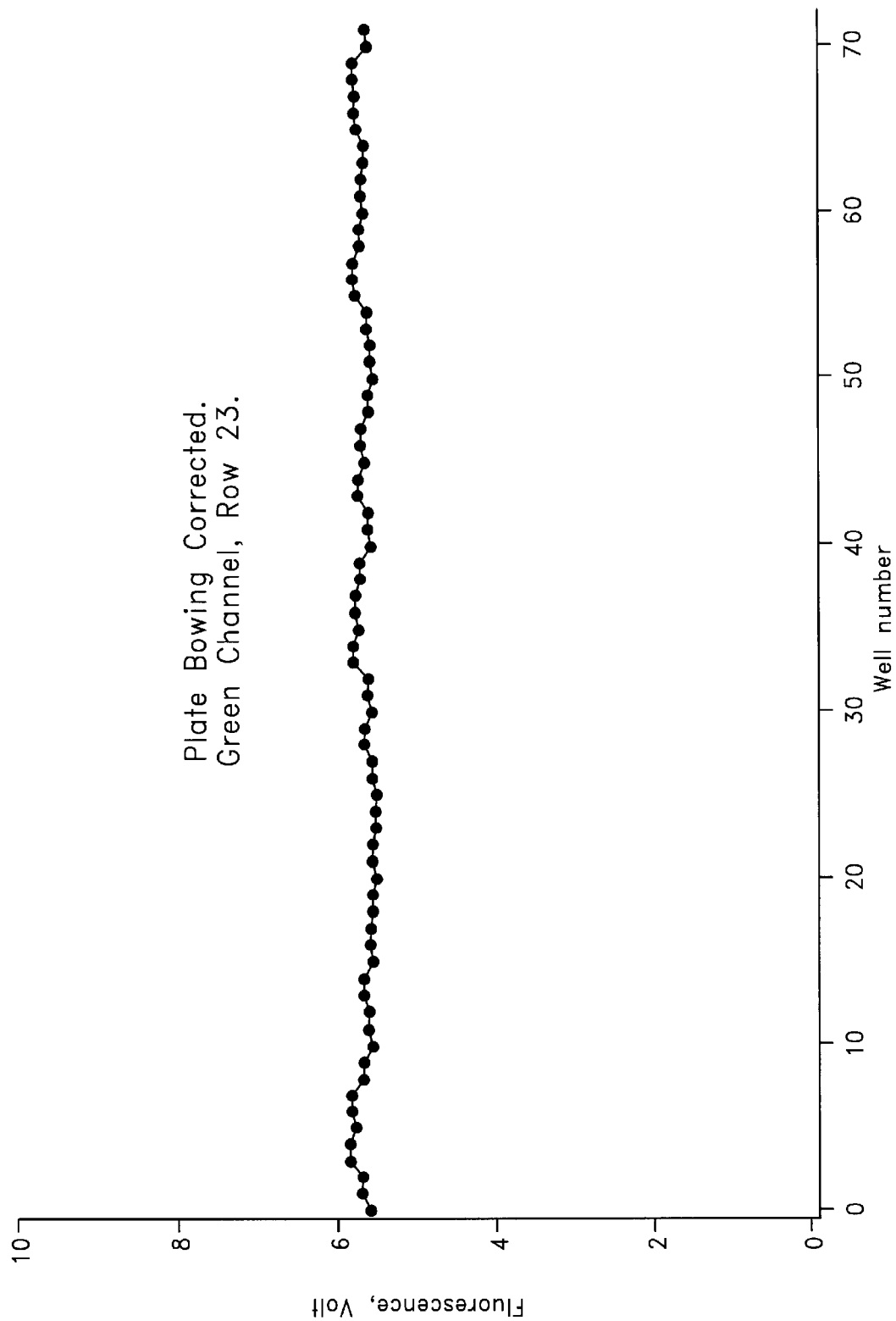
FIG. 26 is a plot of collected light intensity for a scan of all 72 wells of row 23 of a 3456-well plate with the optics vertical profiling activated.
Figure 27:
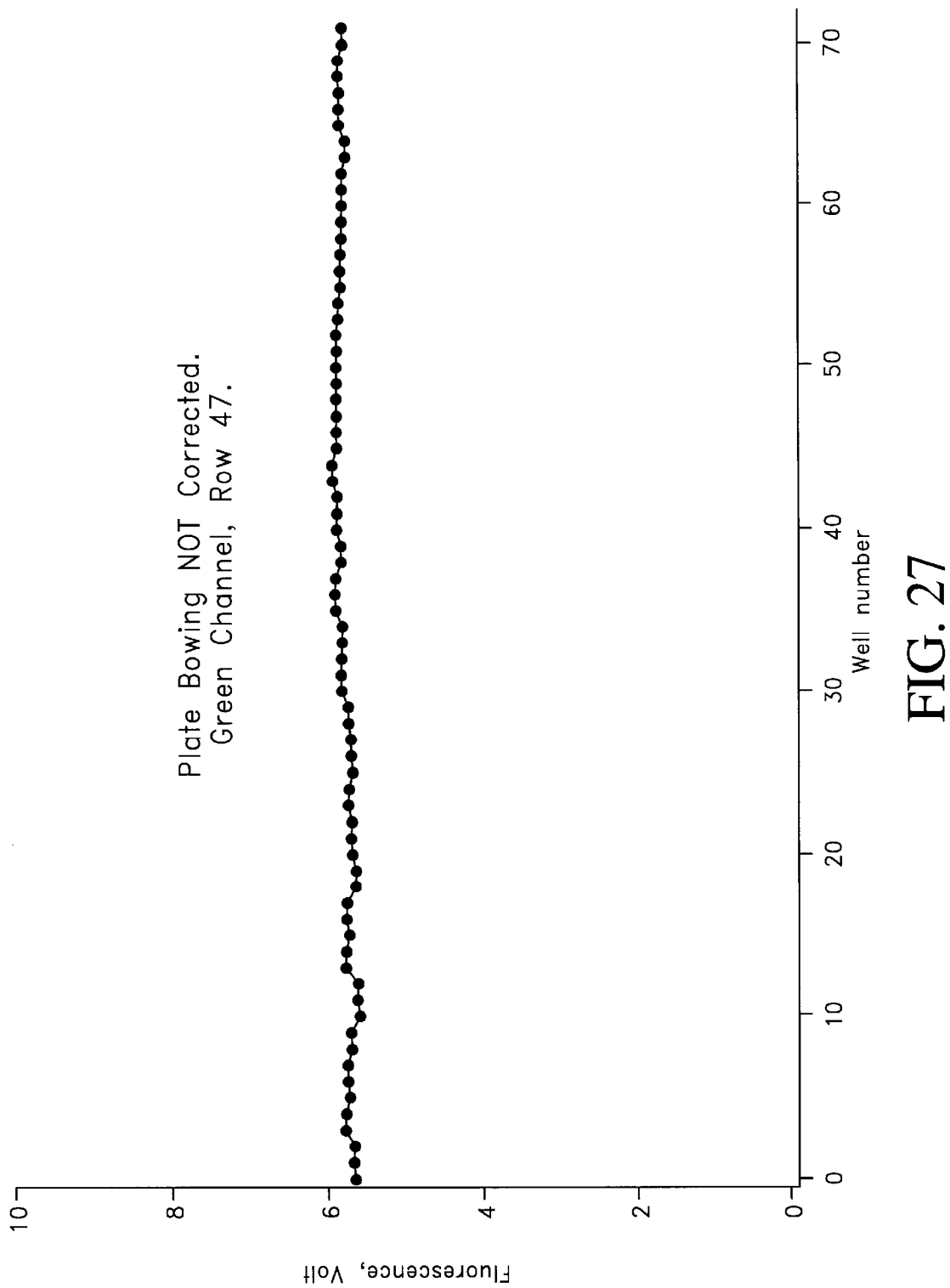
FIG. 27 is a plot of collected light intensity for a scan of all 72 wells of row 47 of a 3456-well plate with the optics vertical profiling deactivated.
Figure 28:
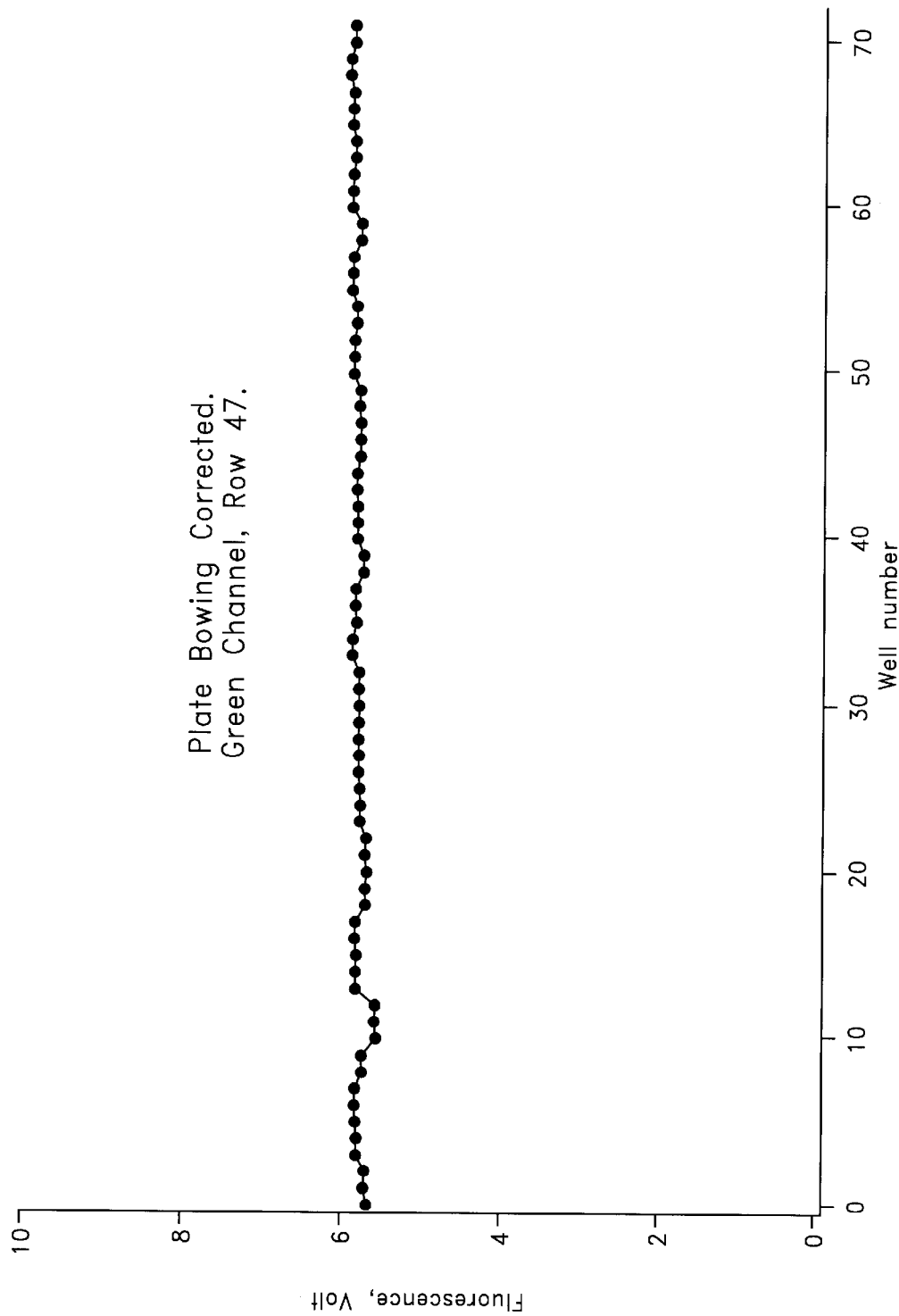
FIG. 28 is a plot of collected light intensity for a scan of all 72 wells of row 47 of a 3456-well plate with the optics vertical profiling activated.

The improvement in reading fluorescent data in the wells of the plate 30 was also demonstrated. First, a 3456-well plate containing the same amount of fluoroscein in all 3456 wells was scanned without using the method of compensating for varying elevation in the bottom surface of the plate (i.e. without adjusting the vertical position of the optics 37). The data from the first scan is shown in FIG. 21. There is a significant level of variation and scatter in the data as evidenced by the coefficient of variance (CV) being at 15%. FIG. 22 shows a scan of the same plate using the compensation method described above. It is clear that there is a significant decrease in the variation of the measurements and the CV has fallen to 2.1%. FIGS. 23 through 28 show this same comparison for the scans of the three individual rows 0, 23 and 47. Again, these results verify that the compensation method significantly improves the quality of the measurements obtained from a multiwell plate.

A second method of reading the plate 30 while compensating for variations in the elevation of the bottom surface 31 comprises detecting the elevation of the bottom surface 31 and adjusting the height of the optics 37 during the scan of the wells of the multiwell plate 30. With this method, the sensor 103 is precisely located forward in the path of the optics 37 in a first direction of the movement of the plate relative to the optics 37. A second sensor (not shown) is located forward in the path of the optics 37 in a second direction opposite the first direction. In this way, the two sensors can measure the elevation of the bottom surface 31 prior to the optics reaching the location of the sensors, one sensor for each direction of the movement of the plate 30 relative to the optics 37 in the raster scan pattern as shown in FIG. 5. If the scan pattern includes movement of the plate in additional directions, more sensors can be added to measure the elevation of the bottom surface 31 during movement in those directions.

With this configuration, the appropriate sensor for the particular direction of plate movement measures the elevation of the bottom surface 31 a determinable time and/or distance prior to the optics 37 reaching that location. The elevation data is used to compute a profile similar to that described above, except that the profile only includes one or a few of the segments along a row of wells rather than the entire row as described above. This data is normalized using the same or similar calibration method as described above and then the resulting data is loaded into the controller. The controller signals the vertical stage 101 to adjust the height of the optics 37 according to the profile to maintain a substantially constant distance between the bottom surface 31 and the optics 37. This second method eliminates the prescan of the bottom surface 31 of the first method described above.

The present invention contemplates other configurations and methods for detecting and compensating for platform characteristics other than the distance between a detector and a plate bottom. For instance, a sensor can be provided to detect the top of the wells of a multiwell plate, the surface of a solution contained in each of the wells, or a marker located in each well, or the transmittance or thickness of the bottom of the plate, etc. Data from the sensor is then analyzed and processed to create a compensation scheme. A parameter of the scanner is then adjusted according to the scheme to compensate for the detected characteristic of the platform.

The present invention contemplates that the scanning apparatus and method can be utilized with a large variety of multiwell plate formats, as well as other sample measurement formats. For example, multiwell plates may be orientated and configured in a variety of designs and formats and be present either with, or without, lids. Multiwell plates, commonly known as "microplates", have been in common use for decades with a predominant format being a molded plastic multiwell plate having 96 sample wells in an 8×12 rectangular array. Typical well volumes are 200 or 300 microliters, depending upon the manufacturer and model of multiwell plate, although other volumes may be provided for specific uses, for example see Whatman/Polyfiltronics 1998 *Microplate Product Guide*. Polyfiltronics Inc., 136 Weymouth Street, Rockland, Mass. 02370 USA. A proposed standard, designated *"Microplate 96-Well Standard"* (MP96) has been promulgated by The Society for Biomolecular Screening, as published in Journal of Biomolecular Screening, Volume 1, Number 4, 1996, the disclosure of which is incorporated herein by reference. A multiwell plate which meets the general dimensional requirements of the standard is designated MP96-3. One of the advantages of the present invention is that the scanner is readily compatible with virtually any format of multiwell plate irrespective of the well density.

Multiwell plates are used for many different types of applications, including chemical library generation and storage, additionally multiwell plates may also be used to hold arrays of polynucleotides for use in expression analysis, or genomic analysis, as described in for example, Schena (1996) *Genome analysis with gene expression microarrays* BioEssays 18 no 5 427–431; Johnson (1998), *Gene chips: Array of hope for understanding gene regulation* Current Biology 8 R171–R174; Scholler et al. (1998) *Optimization and automation of fluorescence-based DNA hybridization for high-throughput clone mapping* Electrophoresis 19 504–508. Multiwell plates may also be used for gene amplification using the polymerase chain reaction as described in U.S. Pat. No. 5,545,528 entitled *Rapid Screening Method of Gene Amplification Products in Polypropylene Plates*. Fluorescence based applications for multiwell plates such as these would be suitable with the present inventions.

The advent of high throughput analysis and increasing use of miniaturized formats has also lead to the development of higher format multiwell plates for example, 384, 864 and 3456 wells as described in PCT patent application identified by serial number PCT/US98/11061 entitled *Low Background Multi-Well Plates With Greater Than 864 Wells for Fluorescence Measurements of Biological and Biochemical Samples*, published Dec. 2, 1998. Even higher density sample processing systems, for example using chips that contain miniaturized microfluidic devices are being developed (see for example, Marshall (1998) *Lab-on-a Chip: Biotech's Next California Gold Rush* R & D Magazine, November 1998, pages 38 to 43). These miniaturized microfludic systems are readily amenable to detection using the present method.

In another embodiment, the system can measure a two dimensional array of samples, such as optical probes dispersed on a substratum, for example as described in U.S. Pat. No. 4,216,245 issued Aug. 5, 1980 to Johnson, U.S. Pat. No.

5,721,435 issued Feb. 24, 1998 to Troll, and U.S. Pat. No. 5,601,980 issued Feb. 11, 1997 issued to Gordon et al. Such an approach provides the ability to rapidly profile large numbers of optical probes and or large numbers of samples in a simple, miniaturized high throughput format.

In another aspect of the present invention, many different assays can be employed with the devices and methods disclosed herein, such as biochemical and cell based assays. Fluorescent probes can be substrates for enzymes, dyes, fluorescent proteins and any other moiety that can produce a fluorescent signal under the appropriate conditions. For example, probes described in PCT application PCT US95/14692 (Tsien), PCT application PCT US96/04059 (Tsien), PCT application PCT US96/09652 (Tsien), U.S. patent application Ser. No., 08/680,877 (Tsien and Cubitt), U.S. patent application Ser. No., 08/706,408, (Tsien), and U.S. patent application Ser. No. 09/301,525 can be used.

Fluorescence Measurements

It is recognized that different types of fluorescent monitoring systems can be used to practice the invention with fluorescent probes, such as fluorescent dyes or substrates. Preferably, systems dedicated to high throughput screening, e.g., 96-well or greater microtiter plates, are used. Methods of performing assays on fluorescent materials are well known in the art and are described in, e.g., Lakowicz, J. R., *Principles of Fluorescence Spectroscopy*, New York: Plenum Press (1983); Herman, B., Resonance Energy Transfer Microscopy, in: *Fluorescence Microscopy of Living Cells in Culture, Part B, Methods in Cell Biology*, vol. 30, ed. Taylor, D. L. & Wang, Y.-L., San Diego: Academic Press (1989), pp. 219–243; Turro, N.J., *Modern Molecular Photochemistry*, Menlo Park: Benjamin/Cummings Publishing Col, Inc. (1978), pp. 296–361 and the Molecular Probes Catalog (1997), OR, USA.

Fluorescence in a sample can be measured using a detector described herein or known in the art for multi-well platforms. In general, excitation radiation from an excitation source having a first wavelength, passes through excitation optics. The excitation optics causes the excitation radiation to excite the sample. In response, fluorescent probes in the sample emit radiation that has a wavelength that is different from the excitation wavelength. Collection optics then collect the emission from the sample. The device can include a temperature controller to maintain the sample at a specific temperature while it is being scanned. According to one embodiment, a multi-axis translation stage (e.g., a dedicated X,Y positioner) moves a multi-well platform holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

Preferably, FRET (fluorescence resonance energy transfer) is used as a way of monitoring probes in a sample (cellular or biochemical). The degree of FRET can be determined by any spectral or fluorescence lifetime characteristic of the excited construct, for example, by determining the intensity of the fluorescent signal from the donor, the intensity of fluorescent signal from the acceptor, the ratio of the fluorescence amplitudes near the acceptor's emission maxima to the fluorescence amplitudes near the donor's emission maximum, or the excited state lifetime of the donor. For example, cleavage of the linker increases the intensity of fluorescence from the donor, decreases the intensity of fluorescence from the acceptor, decreases the ratio of fluorescence amplitudes from the acceptor to that from the donor, and increases the excited state lifetime of the donor.

Preferably, changes in signal are determined as the ratio of fluorescence at two different emission wavelengths, a process referred to as "ratioing." Differences in the absolute amount of probe (or substrate), cells, excitation intensity, and turbidity or other background absorbances between addressable wells can affect the fluorescence signal. Therefore, the ratio of the two emission intensities is a more robust and preferred measure of activity than emission intensity alone.

A ratiometric fluorescent probe system can be used with the invention. For instance the reporter system described in PCT publication WO96/30540 (Tsien and Zlokarnik) has significant advantages over existing reporters for gene expression analysis, as it allows sensitive detection and isolation of both expressing and non-expressing single living cells. This assay system uses a non-toxic, non-polar fluorescent substrate that is easily loaded and then trapped intracellularly. Cleavage of the fluorescent substrate by β-lactamase yields a fluorescent emission shift as substrate is converted to product. Because the β-lactamase reporter readout is ratiometric, it is unique among reporter gene assays in that it controls variables such as the amount of substrate loaded into individual cells. The stable, easily detected, intracellular readout simplifies assay procedures by eliminating the need for washing steps, which facilitates miniaturized screening with cells using the invention.

Methods for Detecting the Presence of an Analyte in a Sample

A method of the present invention uses targets for detecting the presence of an analyte, such as chemicals that are useful in modulating the activity of a target, in a sample. Typically, as discussed below targets can be proteins such as cell surface proteins or enzymes. A biological process or a target can be assayed in either biochemical assays (targets free of cells), or cell based assays (targets associated with a cell). This method can also be used to identify a modulator of a biological process or target in a sample. This method detects the presence of an using the apparatus and scanning methods of the present invention by detecting light emitted from the sample. The method comprises the steps of: exciting at least one sample with radiation of a first wavelength, wherein at least one sample suspected of containing an analyte is placed into at least one well of a multi-well platform of the present invention, which can contain a biological process or target. The sample and biological process or target can be contacted within the well, or outside of the well and later placed within the well. The emission of radiation of a second wavelength emitted from the sample is measured, wherein the amount of radiation of a second wavelength measured indicates the presence or absence of the analyte in the sample.

Targets can be cells, which may be loaded with ion or voltage sensitive dyes to report receptor or ion channel activity, such as calcium channels or N-methyl-D-aspartate (NMDA) receptors, GABA receptors, kainate/AMPA receptors, nicotinic acetylcholine receptors, sodium channels, calcium channels, potassium channels excitatory amino acid (EAA) receptors, nicotinic acetylcholine receptors. Assays for determining activity of such receptors can also use agonists and antagonists to use as negative or positive controls to assess activity of tested chemicals. In preferred embodiments of automated assays for identifying chemicals that have the capacity to modulate the function of receptors or ion channels (e.g., agonists, antagonists), changes in the level of ions in the cytoplasm or membrane voltage will be monitored using an ion-sensitive or membrane voltage fluorescent indicator, respectively. Among the ion-sensitive indicators and voltage probes that may be employed, are those disclosed in the Molecular Probes 1997 Catalog, herein incorporated by reference.

Other methods of the present invention concern determining the activity of receptorsin the presence of a test chemical. Receptor activation typically initiates subsequent intracellular events such as the release of intracellular stores of calcium ions or other second messenger. Activation of some G-protein-coupled receptors (GCPRs) stimulates the formation of inositol triphosphate ($IP_3$ a G-protein coupled receptor second messenger) through phospholipase C-mediated hydrolysis of phosphatidylinositol 4,5-bisphosphate, Berridge and Irvine (1984), Nature 312: 315–21. $IP_3$ in turn stimulates the release of intracellular calcium stores. Thus, a change in cytoplasmic calcium ion levels caused by release of calcium ions from intracellular stores can be used to reliably determine G-protein-coupled receptor function. Among G-protein-coupled receptors are muscarinic acetylcholine receptors (mAChR), adrenergic receptors, serotonin receptors, dopamine receptors, angiotensin receptors, adenosine receptors, bradykinin receptors, metabotropic excitatory amino acid receptors and the like. Cells expressing such G-protein-coupled receptors may exhibit increased cytoplasmic calcium levels as a result of contribution from both intracellular stores and via activation of plasma membrane ion channels, in which case it may be desirable, although not necessary, to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP or cGMP. For example, activation of some dopamine, serotonin, metabotropic glutamate receptors and muscarinic acetylcholine receptors results in a decrease in the cAMP or cGMP levels of the cytoplasm. Furthermore, there are cyclic nucleotide-gated ion channels, e.g., rod photoreceptor cell channels and olfactory neuron channels (see, Altenhofen, W. et al. (1991) Proc. Natl. Acad. Sci U.S.A. 88: 9868–9872 and Dhallan et al. (1990) Nature 347: 184–187) that are permeable to cations upon activation by binding of cAMP or cGMP. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-gated ion channel and DNA encoding a receptor (e.g., certain metabotropic glutamate receptors, muscarinic acetylcholine receptors, dopamine receptors, serotonin receptors, and the like), which, when activated, cause a change in cyclic nucleotide levels in the cytoplasm.

Any cell expressing a protein target in sufficient quantity for measurement in a cellular assay can be used with the invention. Cells endogenously expressing a protein can work as well as cells expressing a protein from heterologous nucleic acids. For example, cells may be transfected with a suitable vector encoding one or more such targets that are known to those of skill in the art or may be identified by those of skill in the art. Although essentially any cell which expresses an endogenous ion channel or receptor activity may be used, when using receptors or channels as targets it is preferred to use cells transformed or transfected with heterologous DNAs encoding such ion channels and/or receptors so as to express predominantly a single type of ion channel or receptor. Many cells that can be genetically engineered to express a heterologous cell surface protein are known. Such cells include, but are not limited to, baby hamster kidney (BHK) cells (ATCC No. CCL10), mouse L cells (ATCC No. CCLI.3), Jurkats (ATCC No. TIB 152) and 153 DG44 cells (see, Chasin (1986) Cell. Molec. Genet. 12: 555) human embryonic kidney (HEK) cells (ATCC No. CRL1573), Chinese hamster ovary (CHO) cells (ATCC Nos. CRL9618, CCL61, CRL9096), PC12 cells (ATCC No. CRL17.21) and COS-7 cells (ATCC No. CRL1651). Preferred cells for heterologous cell surface protein expression are those that can be readily and efficiently transfected. Preferred cells include Jurkat cells and HEK 293 cells, such as those described in U.S. Pat. No. 5,024,939 and by Stillman et al. (1985) Mol. Cell. Biol. 5: 2051–2060.

Exemplary membrane proteins include, but are not limited to, surface receptors and ion channels. Surface receptors include, but are not limited to, muscarinic receptors, e.g., human M2 (GenBank accession #M16404); rat M3 (GenBank accession #M16407); human M4 (GenBank accession #M16405); human M5 (Bonner, et al., (1988) Neuron 1, pp. 403–410); and the like. Neuronal nicotinic acetylcholine receptors include, but are not limited to, e.g., the human $\alpha_2$, $\alpha_3$, and $\beta_2$, subtypes disclosed in U.S. Ser. No. 504,455 (filed Apr. 3, 1990, which is hereby expressly incorporated by reference herein in its entirety); the human $\alpha_5$ subtype (Chini, et al. (1992) Proc. Natl. Acad. Sci. U.S.A. 89: 1572–1576), the rat $\alpha_2$ subunit (Wada, et al. (1988) Science 240, pp. 330–334); the rat $\alpha_3$ subunit (Boulter, et al. (1986) Nature 319, pp. 368–374); the rat $\alpha_4$ subunit (Goldman, et al. (1987) Cell 48, pp. 965–973); the rat $\alpha_5$ subunit (Boulter, et al. (1990) J. Biol. Chem. 265, pp. 4472–4482); the chicken $\alpha_7$ subunit (Couturier et al. (1990) Neuron 5: 847–856); the rat $\beta_2$ subunit (Deneris, et al. (1988) Neuron 1, pp. 45–54) the rat $\beta_3$ subunit (Deneris, et al. (1989) J. Biol. Chem. 264, pp. 6268–6272); the rat $\beta_4$ subunit (Duvoisin, et al. (1989) Neuron 3, pp. 487–496); combinations of the rat $\alpha$ subunits, $\beta$ subunits and a and p subunits; GABA receptors, e.g., the bovine n and p subunits (Schofield, et al. (1987) Nature 328, pp. 221–227); the bovine n, and a, subunits (Levitan, et al. (1988) Nature 335, pp. 76–79); the $\gamma$-subunit (Pritchett, et al. (1989) Nature 338, pp. 582–585); the p, and p, subunits (Ymer, et al. (1989) EMBO J. 8, pp. 1665–1670); the 6 subunit (Shivers, B. D. (1989) Neuron 3, pp. 327–337); and the like. Glutamate receptors include, but are not limited to, e.g., rat GluR1 receptor (Hollman, et al. (1989) Nature 342, pp. 643–648); rat GluR2 and GluR3 receptors (Boulter et al. (1990) Science 249:1033–1037; rat GluR4 receptor (Keinanen et al. (1990) Science 249: 556–560); rat GluR5 receptor (Bettler et al. (1990) Neuron 5: 583–595) g rat GluR6 receptor (Egebjerg et al. (1991) Nature 351: 745–748); rat GluR7 receptor (Bettler et al. (1992) neuron 8:257–265); rat NMDAR1 receptor (Moriyoshi et al. (1991) Nature 354:31–37 and Sugihara et al. (1992) Biochem. Biophys. Res. Comm. 185:826–832); mouse NMDA e1 receptor (Meguro et al. (1992) Nature 357: 70–74); rat NMDAR2A, NMDAR2B and NMDAR2C receptors (Monyer et al. (1992) Science 256: 1217–1221); rat metabotropic mGluR1 receptor (Houamed et al. (1991) Science 252: 1318–1321); rat metabotropic mGluR2, mGluR3 and mGluR4 receptors (Tanabe et al. (1992) Neuron 8:169–179); rat metabotropic mGluR5 receptor (Abe et al. (1992) J. Biol. Chem. 267: 13361–13368); and the like. Adrenergic receptors include, but are not limited to, e.g., human p1 (Frielle, et al. (1987) Proc. Natl. Acad. Sci. 84, pp. 7920–7924); human $\alpha_2$ (Kobilka, et al. (1987) Science 238, pp. 650–656); hamster $\beta_2$ (Dixon, et al. (1986) Nature 321, pp. 75–79); and the like. Dopamine receptors include, but are not limited to, e.g., human D2 (Stormann, et al. (1990) Molec. Pharm. 37, pp. 1–6); mammalian dopamine D2 receptor (U.S. Pat. No. 5,128,254); rat (Bunzow, et al. (1988) Nature 336, pp. 783–787); and the like. NGF receptors include, but are not limited to, e.g., human NGF receptors (Johnson, et al. (1986) Cell 47, pp. 545–554); and the like. Serotonin receptors include, but are not limited to, e.g., human 5HT1a (Kobilka, et al. (1987) Nature 329, pp. 75–79); serotonin 5HT1C receptor (U.S. Pat. No. 4,985,352); human 5HT1D (U.S. Pat. No. 5,155,218); rat 5HT2 (Julius, et al. (1990) PNAS 87, pp. 928–932); rat 5HT1c (Julius, et al. (1988) Science 241, pp. 558–564); and the like.

Ion channels include, but are not limited to, calcium channels comprised of the human calcium channel $\alpha_2\beta$ and/or $\gamma$-subunits disclosed in commonly owned U.S. application Ser. Nos. 07/745,206 and 07/868,354, filed Aug. 15, 1991 and Apr. 10, 1992, respectively, the contents of which are hereby incorporated by reference; (see also, WO89/09834; human neuronal $\alpha_2$ subunit); rabbit skeletal muscle al subunit (Tanabe, et al. (1987) Nature 328, pp. 313–E318); rabbit skeletal muscle $\alpha_2$ subunit (Ellis, et al. (1988) Science 241, pp. 1661–1664); rabbit skeletal muscle p subunit (Ruth, et al. (1989) Science 245, pp. 1115–1118); rabbit skeletal muscle $\gamma$ subunit (Jay, et al. (1990) Science 248, pp. 490–492); and the like. Potassium ion channels include, but are not limited to, e.g., rat brain (BK2) (McKinnon, D. (1989) J. Biol Chem. 264, pp. 9230–8236); mouse brain (BK1) (Tempel, et al. (1988) Nature 332, pp. 837–839); and the like. Sodium ion channels include, but are not limited to, e.g., rat brain I and II (Noda, et al. (1986) Nature 320, pp. 188–192); rat brain III (Kayano, et al. (1988) FEBS Lett. 228, pp. 187–1.94); human II (ATCC No. 59742, 59743 and Genomics 5: 204–208 (1989); chloride ion channels (Thiemann, et al. (1992), Nature 356, pp. 57–60 and Paulmichl, et al. (1992) Nature 356, pp. 238–241), and others known or developed in the art.

Intracellular receptors may also be used as targets, such as estrogen receptors, glucocorticoid receptors, androgen receptors, progesterone receptors, and mineralocorticoid receptors, in the invention. Transcription factors and kinases can also be used as targets, as well as plant targets.

Various methods of identifying activity of chemical with respect to a target can be applied, including: ion channels (PCT publication WO 93/13423) and intracellular receptors (PCT publication WO 96/41013, U.S. Pat. No. 5,548,063, U.S. Pat. Nos. 5,171,671, 5,274,077, 4,981,784, EP 0 540 065 A1, U.S. Pat. Nos. 5,071,773, and 5,298,429). All of the foregoing references are herein incorporated by reference in their entirety.

If the analyte is present in the sample, then the target will exhibit increased or decreased fluorescence. Such fluorescence can be detected using the methods of the present invention by exciting the sample with radiation of a first wavelength, which excites a fluorescent reporter in the sample, which emits radiation of a second wavelength, which can be detected. The amount of the emission is measured, and compared to proper control or background values. The amount of emitted radiation that differs from the background and control levels, either increased or decreased, correlates with the amount or potency of the analyte in the sample. Standard curves can be determined to make the assay more quantitative.

Testing a Therapeutic for Therapeutic Activity and Toxicology

The present invention also provides a method for testing a therapeutic for therapeutic activity and toxicology. A therapeutic is identified by contacting a test chemical suspected of having a modulating activity of a biological process or target with a biological process or target utilizing the apparatus and methods of the present invention. If the sample contains a modulator, then the amount of a fluorescent reporter product in the sample, such as inside or outside of the cell, will either increase or decrease relative to background or control levels. The amount of the fluorescent reporter product is measured by exciting the fluorescent reporter product with an appropriate radiation of a first wavelength and measuring the emission of radiation of a second wavelength emitted from said sample. The amount of emission is compared to background or control levels of emission. If the sample having the test chemical exhibits increased or decreased emission relative to that of the control or background levels, then a candidate modulator has been identified. The amount of emission is related to the amount or potency of the therapeutic in the sample. Such methods are described in, for example, Tsien (PCT/US90/04059) The candidate modulator can be further characterized and monitored for structure, potency, toxicology, and pharmacology using well known methods.

The structure of a candidate modulator identified by the invention can be determined or confirmed by methods known in the art, such as mass spectroscopy. For putative modulators stored for extended periods of time, the structure, activity, and potency of the putative modulator can be confirmed.

Depending on the system used to identify a candidate modulator, the candidate modulator will have putative pharmacological activity. For example, if the candidate modulator is found to inhibit T-cell proliferation (activation) in vitro, then the candidate modulator would have presumptive pharmacological properties as an immunosuppressant or anti-inflammatory (see, Suthanthiran et al., *Am. J. Kidney Disease*, 28:159–172 (1996)). Such nexuses are known in the art for several disease states, and more are expected to be discovered over time. Based on such nexuses, appropriate confirmatory in vitro and in vivo models of pharmacological activity, as well as toxicology, can be selected. The methods described herein can also be used to assess pharmacological selectivity and specificity, and toxicity.

Toxicology of Candidate Modulators

Once identified, candidate modulators can be evaluated for toxicological profiling, or example via the analysis of their susceptibility to metabolism by cytochrome P450 enzymes, for example using the fluorescent cytochrome P450 substrates as described in commonly assigned U.S. application serial number 09/301,525.

The cytochrome P450 enzyme (CYP450) family comprises oxidase enzymes involved in the xenobiotic metabolism of hydrophobic drugs, carcinogens, and other potentially toxic compounds and metabolites circulating in blood. It is known that the liver is the major organ for xenobiotic metabolism, containing high levels of the most important CYP450 mixed-function oxygenases. There are numerous human P450 enzyme sub-families, often termed "isozymes" or "isoforms." Those of the CYP 3A4, CYP 2D6, CYP 2C, CYP 2A1 and CYP 2E1 subfamilies are known to be important in drug metabolism. See, e.g., Murray, M., 23 Clin. Pharmacokinetics 132–46 (1992). Of these isoforms, CYP 3A4 is by far the major isoform in liver and the small intestines, comprising 30% and 70% respectively of the total CYP450 protein in those tissues. Based primarily on in vitro studies, it has been estimated that the metabolism of 40% to 50% of all drugs used in humans involve CYP 3A4 catalyzed oxidations. See Thummel, K. E. & Wilkinson, G. R., *In Vitro and In Vivo Drug Interactions Involving Human CYP 3A*, 38 Ann. Rev. Pharmacol. Toxicol., 389–430 (1998). Efficient metabolism of a candidate drug by a CYP450 enzyme may lead to poor pharmacokinetic properties, while drug candidates that act as potent inhibitors of a CYP450 enzyme can cause undesirable drug-drug interactions when administered with another drug that interacts with the same CYP450 . See, e.g., Peck, C. C. et al., *Understanding Consequences of Concurrent Therapies,* 269 JAMA 1550–52 (1993). Accordingly, early, reliable indication that a candidate drug interacts with (i.e., is a substrate or inhibitor of) a CYP450 may greatly shorten the discovery cycle of pharmaceutical research and development, and thus may reduce the time required to market the candidate drug. Consequently, such earlier-available, reliable CYP450 pharmokinetic information may result in greatly reduced drug development costs and/or increased profits from earlier market entrance. Furthermore, such earlier-available, reliable CYP450 pharmokinetic information may allow a candidate drug to reach the public sooner, at lower costs than otherwise feasible. Accordingly, extensive pharmacokinetic studies of drug interactions in humans have recently become an integral part of the pharmaceutical drug development and safety assessment process. See, e.g., Parkinson, A., 24 Toxicological Pathology 45–57 (1996). The present invention provides for (1) the more rapid acquisition of information about drug candidate interactions with CYP450 enzymes, earlier in the drug discovery process than presently feasible, and hence will allow for (2) the earlier elimination of unsuitable compounds and chemical series from further development efforts.

In addition, once identified, candidate modulators can be evaluated for toxicological effects using known methods (see, Lu, *Basic Toxicology. Fundamentals, Target Organs, and Risk Assessment*, Hemisphere Publishing Corp., Washington (1985); U.S. Pat. No: 5,196,313 to Culbreth (issued Mar. 23, 1993) and U.S. Pat. No. 5,567,952 to Benet (issued Oct. 22, 1996). For example, toxicology of a candidate modulator can be established by determining in vitro toxicity towards a cell line, such as a mammalian i.e. human, cell line. Candidate modulators can be treated with, for example, tissue extracts, such as preparations of liver, such as microsomal preparations, to determine increased or decreased toxicological properties of the chemical after being metabolized by a whole organism. The results of these types of studies are often predictive of toxicological properties of chemicals in animals, such as mammals, including humans.

Alternatively, or in addition to these in vitro studies, the toxicological properties of a candidate modulator in an animal model, such as mice, rats, rabbits, or monkeys, can be determined using established methods (see, Lu, supra (1985); and Creasey, *Drug Disposition in Humans, The Basis of Clinical Pharmacology*, Oxford University Press, Oxford (1979)). Depending on the toxicity, target organ, tissue, locus, and presumptive mechanism of the candidate modulator, the skilled artisan would not be burdened to determine appropriate doses, $LD_{50}$ values, routes of administration, and regimes that would be appropriate to determine the toxicological properties of the candidate modulator. In addition to animal models, human clinical trials can be performed following established procedures, such as those set forth by the United States Food and Drug Administration (USFDA) or equivalents of other governments. These toxicity studies provide the basis for determining the efficacy of a candidate modulator in vivo.

Efficacy of Candidate Modulators

Efficacy of a candidate modulator can be established using several art recognized methods, such as in vitro methods, animal models, or human clinical trials (see, Creasey, supra (1979)). Recognized in vitro models exist for several diseases or conditions. For example, the ability of a chemical to extend the life-span of HIV-infected cells in vitro is recognized as an acceptable model to identify chemicals expected to be efficacious to treat HIV infection or AIDS (see, Daluge et al., *Antimicro. Agents Chemother.* 41:1082–1093 (1995)). Furthermore, the ability of cyclosporin A (CsA) to prevent proliferation of T-cells in vitro has been established as an acceptable model to identify chemicals expected to be efficacious as immunosuppressants (see, Suthanthiran et al., supra, (1996)). For nearly every class of therapeutic, disease, or condition, an acceptable in vitro or animal model is available. Such models exist, for example, for gastro-intestinal disorders, cancers, cardiology, neurobiology, and immunology. In addition, these in vitro methods can use tissue extracts, such as preparations of liver, such as microsomal preparations, to provide a reliable indication of the effects of metabolism on the candidate modulator. Similarly, acceptable animal models may be used to establish efficacy of chemicals to treat various diseases or conditions. For example, the rabbit knee is an accepted model for testing chemicals for efficacy in treating arthritis (see, Shaw and Lacy, *J. Bone Joint Surg. (Br)* 55:197–205 (1973)). Hydrocortisone, which is approved for use in humans to treat arthritis, is efficacious in this model which confirms the validity of this model (see, McDonough, *Phys. Ther.* 62:835–839 (1982)). When choosing an appropriate model to determine efficacy of a candidate modulator, the skilled artisan can be guided by the state of the art to choose an appropriate model, dose, and route of administration, regime, and endpoint and as such would not be unduly burdened In addition to animal models, human clinical trials can be used to determine the efficacy of a candidate modulator in humans. The USFDA, or equivalent governmental agencies, have established procedures for such studies.

Selectivity of Candidate Modulators

The in vitro and in vivo methods described above also establish the selectivity of a candidate modulator. It is recognized that chemicals can modulate a wide variety of biological processes or be selective. Panels of cells based on the present invention can be used to determine the specificity of the candidate modulator. Selectivity is evident, for example, in the field of chemotherapy, where the selectivity of a chemical to be toxic towards cancerous cells, but not towards non-cancerous cells, is obviously desirable. Selective modulators are preferable because they have fewer side effects in the clinical setting. The selectivity of a candidate modulator can be established in vitro by testing the toxicity and effect of a candidate modulator on a plurality of cell lines that exhibit a variety of cellular pathways and sensitivities. The data obtained from these in vitro toxicity studies can be extended animal model studies, including human clinical trials, to determine toxicity, efficacy, and selectivity of the candidate modulator.

Identified Compositions

The invention includes compositions such as novel chemicals, and therapeutics identified as having activity by the operation of methods, systems or components described herein. Novel chemicals, as used herein, do not include chemicals already publicly known in the art as of the filing date of this application. Typically, a chemical would be identified as having activity from using the invention and then its structure revealed from a proprietary database of chemical structures or determined using analytical techniques such as mass spectroscopy.

One embodiment of the invention is a chemical with useful activity, comprising a chemical identified by the method described above. Such compositions include small organic molecules, nucleic acids, peptides and other molecules readily synthesized by techniques available in the art and developed in the future. For example, the following combinatorial compounds are suitable for screening: peptoids (PCT Publication No. WO 91/19735, Dec. 26, 1991), encoded peptides (PCT Publication No. WO 93/20242, Oct. 14, 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., Proc. Nat. Acad. Sci. USA 90: 6909–6913 (1993)), vinylogous polypeptides (Hagihara et al., J. Amer. Chem. Soc. 114: 6568 (1992)), nonpeptidal peptidomimetics with a Beta-D-Glucose scaffolding (Hirschmann, R. et al., J. Amer. Chem. Soc. 114: 9217–9218 (1992)), analogous organic syntheses of small compound libraries (Chen, C. et al., J. Amer. Chem. Soc. 116:2661 (1994)), oligocarbamates (Cho, C. Y. et al., Science 261: 1303 (1993)), and/or peptidyl phosphonates (Campbell, D. A. et al., J. Org. Chem. 59: 658 (1994)). See, generally, Gordon, E. M. et al., J. Med Chem. 37: 1385 (1994). The contents of all of the aforementioned publications are incorporated herein by reference.

The present invention also encompasses the identified compositions in a pharmaceutical compositions comprising a pharmaceutically acceptable carrier prepared for storage and subsequent administration, which have a pharmaceutically effective amount of the products disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

The compositions of the present invention may be formulated and used as tablets, capsules or elixirs for oral administration; suppositories for rectal administration; sterile solutions, suspensions for injectable administration; and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes), may be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize. In practicing the methods of the invention, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage for the products of the present invention can range broadly depending upon the desired affects and the therapeutic indication. Typically, dosages may be between about 10 mg/kg and 100 mg/kg body weight, preferably between about 100 µg/kg and 10 mg/kg body weight. Administration is preferably oral on a daily basis.

The exact formulation, route of administration and dosage can be chosen by the individual physician in view of the patient's condition. (See e.g., Fingl et al., in The Pharmacological Basis of Therapeutics, 1975). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in Remington's Pharmaceutical Sciences, 18th Ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping, or lyophilizing processes. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dye-stuffs or pigments may be added to the tablets or dragee coatings for identification or to characterize different combinations of active compound doses.

All publications, including patent documents and scientific articles, referred to in this application are incorporated by reference in their entirety for all that they teach and for all purposes as if each individual publication were individually incorporated by reference.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof

What is claimed is:

1. A method of detecting a physico-chemical property of a plurality of samples disposed on a platform, the method comprising:

placing said platform on a detector for detecting said physico-chemical property, said detector having an adjustable parameter;

pre-scanning a portion of said platform to obtain a plurality of measured values of a selected platform characteristic, said measurements made at different locations on said platform;

storing information derived from said pre-scan;

subsequent to said pre-scanning, retrieving said stored information and adjusting said parameter based at least in part on said stored information; and measuring said physico-chemical property of said samples.

2. The method of claim 1, wherein said platform is a multiwell plate.

3. The method of claim 1, wherein said characteristic is a location of a point on said platform relative to a point on said detector and said parameter is the position of a component of said detector.

4. The method of claim 1, wherein said platform is a multiwell plate having a bottom surface and said characteristic is locations of points on said bottom surface relative to an element of said detector.

5. The method of claim 4 wherein said element is a detection head of said detector and said parameter is the distance between said detection head and said bottom surface orthogonal to a plane of said bottom surface and said parameter is adjusted by moving said detection head closer to or further from said bottom surface.

6. The method of claim 4 wherein said element is a detection head of said detector and said parameter is the distance between said detection head and said bottom surface and said parameter is adjusted by moving said multiwell plate closer to or further from said detection head.

7. The method of claim 1, wherein said characteristic is the transmittance of a surface of said platform.

8. The method of claim 1, wherein said physico-chemical property is the fluorescence of said sample and said detector is adapted to measure fluorescence.

9. The method of claim 1, wherein said characteristic is a location of a feature of said platform relative to a sensor on said detector and further comprising:

measuring a platform/detector distance over an area of said platform to obtain a matrix of distances over said area;

calculating from said matrix of distances a profile of said area; and utilizing said profile to control the adjustment of said parameter.

10. In a chemical screening system, a method of scanning a multi-well plate for evidence of chemical activity in one or more wells of said multi-well plate, said method comprising profiling a varying characteristic of said multi-well plate, storing said profile, and adjusting a detector of said chemical activity in accordance with said stored profile during the performance of the scanning operation.

11. The method of claim 10, wherein said varying characteristic comprises the distance between the bottom surface of said multiwell plate and said detector, and wherein said adjusting comprises vertically moving said detector relative to said bottom surface.

12. A method of detecting a physico-chemical property of individual samples contained in a plurality of wells of a multiwell plate comprising:

placing said multiwell plate in a detector adapted to measure said physico-chemical property, said detector having a detection head, an adjustable parameter and a sensor for measuring a feature of said multiwell plate;

making a plurality of measurements with said sensor of said feature at or proximate to a plurality of predetermined locations on said multiwell plate to obtain a measured value of said feature at each of said predetermined locations, each of said predetermined locations being at or proximate to a predetermined well of said multiwell plate;

generating and storing a formula defining said feature as a function of position on said multiwell plate; and measuring with said detector said physico-chemical property of the samples in each predetermined well with the adjustable parameter adjusted based upon the formula.

13. The method of claim 12 wherein each of said measurements of said feature comprises making a plurality of measurements at or proximate each of said predetermined locations.

14. The method of claim 12 wherein all of said measurements of said feature are performed prior to said step of measuring said physico-chemical property.

15. The method of claim 12 wherein said step of measuring said physico-chemical property of the samples comprises continuously moving said multiwell plate relative to said detection head such that said detection head passes a first edge of the predetermined well, passes over the predetermined well, and passes over a second edge of the predetermined well and measuring said physico-chemical property of said sample in the predetermined well during at least a portion of the time said detection head is aligned with said predetermined well.

16. The method of claim 15 wherein said physico-chemical property is an optical property of said sample.

17. The method of claim 12 wherein said feature is a bottom surface of said multiwell plate and said plurality of measurements with said sensor measures the distance between the sensor and said bottom surface.

18. The method of claim 17 wherein said parameter is the distance between said detection head and said bottom surface of the multiwell plate.

19. The method of claim 17 wherein said parameter is adjusted by moving said detection head closer to or further from said bottom surface.

20. The method of claim 19 wherein said physico-chemical property is an optical property of said sample.

21. The method of claim 17 wherein said parameter is adjusted by moving said multiwell plate closer to or further from said detection head.

22. The method of claim 12 wherein said physico-chemical property is an optical property of said sample.

\* \* \* \* \*